United States Patent [19]

Spry

[11] Patent Number: 4,604,386

[45] Date of Patent: Aug. 5, 1986

[54] 3-(ALKYNYLALKYLOXY) CEPHALOSPORINS

[75] Inventor: Douglas O. Spry, Mooresville, Ind.

[73] Assignee: Eli Lilly and Company, Indianapolis, Ind.

[21] Appl. No.: 629,014

[22] Filed: Jul. 9, 1984

[51] Int. Cl.$^4$ .................. A61K 31/545; C07D 501/18; C07D 501/20
[52] U.S. Cl. .................................... 514/200; 514/202; 514/206; 540/215; 540/222; 540/226; 540/227
[58] Field of Search ....................... 514/200, 202, 206; 544/16, 22, 26, 27

[56] References Cited

U.S. PATENT DOCUMENTS 4,073,902 2/1978 Scartazzini ............................ 544/16
4,405,778 9/1983 Scartazzini ............................ 544/22

FOREIGN PATENT DOCUMENTS 1435111 5/1976 United Kingdom .

Primary Examiner—Donald G. Daus
Assistant Examiner—Robert Benson
Attorney, Agent, or Firm—Paul C. Steinhardt

[57] ABSTRACT 3-(alkynylalkyloxy)cephalosporin antibiotics and the intermediates therefor are disclosed. Pharmaceutical compositions for the antibiotics are also disclosed.

59 Claims, No Drawings

3-(ALKYNYLALKYLOXY) CEPHALOSPORINS

SUMMARY OF THE INVENTION

The invention is directed to antibiotic compounds and the corresponding intermediates of the formula:

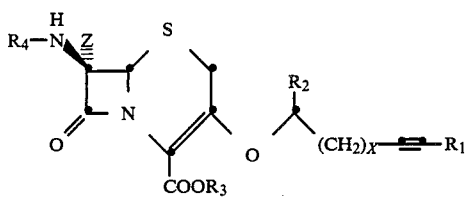

In the above formula, $R_1$, $R_2$, $R_3$, $R_4$, X and Z have the meaning defined for them below.

A further aspect of this invention are pharmaceutical compositions of the antibiotics encompassed by the above formula.

DETAILED DESCRIPTION

This invention relates to antibiotic compounds and corresponding intermediates represented by the following Formula 1:

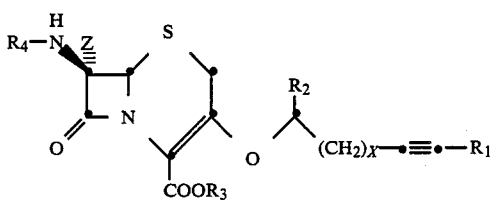

In the above formula, $R_1$ is hydrogen, $C_1$ to $C_4$ alkyl, $C_1$ to $C_4$ alkoxycarbonyl, $C_1$ to $C_4$ alkylthio, phenylthio or halo.

$R_2$ in Formula 1 is hydrogen, $C_1$ to $C_4$ alkyl, phenyl, benzyl or phenethyl. The variable $R_3$ in the above Formula represents hydrogen, a carboxy protecting group, a pharmaceutically acceptable, non-toxic salt of the carboxy group, a hydrate of said salt, or a non-toxic, metabolically labile ester of the carboxy group.

The above $R_4$ is:
(a) hydrogen, or a salt of the amino group;
(b) an amino-protecting group;
(c) a group of the formula:

wherein
$R_5$ is
(i) 1,4-cyclohexadienyl, 1-cyclohexenyl, phenyl or substituted phenyl wherein the substituents are 1 or 2 halogens, hydroxy, protected hydroxy, nitro, $C_1$ to $C_4$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, or N-(methylsulfonylamino);
(ii) an arylalkyl group of the formula $R_6-(y)_m-CH_2-$ wherein y is O or S, m is 0 or 1, $R_6$ is $R_5$ as defined above, and when m is 0, $R_6$ is also 2-thienyl, 3-thienyl, 2-furyl, 3-furyl, 1-tetrazolyl, 5-tetrazolyl, 2-thiazolyl, 2-aminothiazol-4-yl, 2-(protected amino)thiazol-4-yl; or
(iii) a substituted arylalkyl group of the formula

wherein
$R_7$ is $R_6$ as defined above, 2- or 3-indolyl, a substituted 2- or 3-indolyl group of the formula

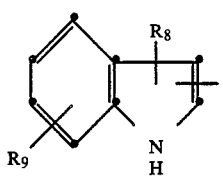

in which
$R_8$ and $R_9$ independently are hydrogen, halo, hydroxy, protected hydroxy, $C_1$ to $C_4$ alkyl, $C_1$ to $C_4$ alkoxy, nitro, amino, protected amino, $C_1$ to $C_4$ alkanoylamino, $C_1$ to $C_4$ alkylsulfonylamino, or when $R_8$ and $R_9$ are on adjacent carbons, they may be taken together to form methylenedioxy, 2- or 3-benzothienyl, a 2- or 3-substituted benzothienyl of the formula

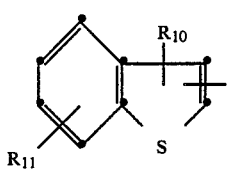

in which
$R_{10}$ and $R_{11}$ are independently hydrogen, halo, hydroxy, protected hydroxy, $C_1$ to $C_4$ alkyl, $C_1$ to $C_4$ alkoxy, nitro, amino, protected amino, $C_1$ to $C_4$ alkanoylamino, $C_1$ to $C_4$ alkylsulfonylamino, and when $R_{10}$ and $R_{11}$ are on adjacent carbon atoms, they can be taken together to form methylenedioxy; 1- or 2-naphthyl, a substituted 1- or 2-naphthyl of the formula

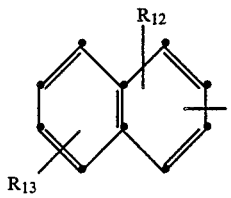

wherein
$R_{12}$ and $R_{13}$ are independently hydrogen, halo, hydroxy, $C_1$ to $C_4$ alkyl, $C_1$ to $C_4$ alkoxy, nitro, amino, protected amino, $C_1$ to $C_4$ alkanoylamino, $C_1$ to $C_4$ alkylsulfonylamino, or when $R_{12}$ and $R_{13}$ are on adjacent carbon atoms, they can be taken together to form methylenedroxy; and W is hydroxy, formyloxy, protected hydroxy, carboxy, a carboxy salt, protected carboxy, amino, a salt of said amino compound, or protected amino; provided that, when W is other than amino, a salt of said amino compound, an amine salt or a protected amino, $R_7$ is other than 2- or 3-indolyl, substituted 2- or 3-indolyl, 2- or 3-benzothienyl, substituted 2- or 3-benzothienyl, 1- or 2-naphthyl, or substituted 1- or 2-naphthyl.

Finally, in the above Formula 1, X is 0 to 4 and Z is hydrogen or methoxy.

In the instant specification, the term "$C_1$ to $C_4$ alkyl" denotes methyl, ethyl, n-propyl, iso-propyl, n-butyl, sec-butyl and tert-butyl.

Examples of the term "$C_1$ to $C_4$ alkoxycarbonyl" include methoxycarbonyl, ethoxycarbonyl, iso-propoxycarbonyl and n-butoxycarbonyl. "$C_1$ to $C_4$ alkylthio" means methylthio, ethylthio, n-propylthio, iso-propylthio, n-butylthio, sec-butylthio and tert-butylthio.

The terms "carboxy-protecting group" and "protected carboxy" as used in the application refer to one of the carboxylic acid substituents commonly employed to block or protect the carboxylic acid functionality while reacting other functional groups on the compound. Examples of such carboxylic acid protecting groups include tert-butyl, 4-methoxybenzyl, benzhydryl (diphenylmethyl), benzyl, para-nitrobenzyl, 2,4,6-trimethoxybenzyl, trityl, 4-methoxytrityl, 4,4'-dimethoxytrityl, and 4,4',4"-trimethoxytrityl and like moieties. The species of carboxy-protecting group employed is not critical so long as the derivatized carboxylic acid is stable to the condition of subsequent reaction(s) on other positions of the cephalosporin molecule and can be removed at the appropriate point without disrupting the remainder of the molecule. Preferred carboxylic acid protecting groups include benzyl, benzhydryl (diphenylmethyl), para-nitrobenzyl and 4-methoxybenzyl, with the more preferred groups being benzhydryl and para-nitrobenzyl. Similar carboxy-protecting groups used in the cephalosporin art are similarly embraced by the above terms. Further examples of these groups are found in E. Haslam in "Protective Groups in Organic Chemistry" J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The term "pharmaceutically acceptable, non-toxic salt of the carboxylate group" or the equivalent term "carboxylate salt" refers to the inorganic salts of the above compounds formed with the alkali and alkaline earth metals such as lithium, sodium, potassium, barium and calcium, organic base salts such as ammonium, dibenzylammonium, benzylammonium, 2-hydroxyethylammonium, bis(2-hydroxyethyl)ammonium, phenylethylbenzylamine, dibenzylethylenediamine, and like salts. Other carboxylate salts encompassed by the above terms include those formed with procaine, quinine and N-methylglusoamine, plus salts formed with basic amino acids such as glycine, ornithine, histidine, phenylglycine, lysine and arginine. Furthermore, the zwitterionic form of the instant compounds formed with a carboxylic acid and amino function, is referred to by these terms. These salts are useful in preparing suitable pharmaceutical compositions of the instant compounds for therapeutic purposes. The preferred pharmaceutically acceptable, non-toxic salt of the carboxylate group are the sodium and potassium salts and the zwitterionic form of the compound.

The hydrates of the above salts are also encompassed in the scope of the instant invention.

The term "non-toxic metabolically labile esters of the carboxylate group" refers to those biologically active ester forms which conduce, for example, to increase the blood levels and prolong the efficacy of the corresponding non-esterified forms of the compounds. Such ester groups include lower alkoxymethyl groups, for example, methoxymethyl, ethoxymethyl, iso-propoxymethyl, $\alpha$-methoxyethyl, groups such as $\alpha$-lower alkoxy ($C_1$ to $C_4$) ethyl; for example methoxyethyl, ethoxyethyl, propoxyethyl, iso-propoxyethyl, etc; 2-oxo-1,3-dioxolen-4-ylmethyl groups, such as 5-methyl-2-oxo-1,3-dioxolen-4-ylmethyl, 5-phenyl-2-oxo-1,3-dioxolen-4-ylmethyl, etc; $C_1$ to $C_3$ alkylthiomethyl groups, for example methylthiomethyl, ethylthiomethyl, isopropylthiomethyl, etc; acyloxymethyl groups, for example pivaloyloxymethyl, $\alpha$-acetoxymethyl, etc; ethoxycarbonyl-1-methyl; or $\alpha$-acyloxy-$\alpha$-substituted methyl groups, for example $\alpha$-acetoxyethyl.

In the present application, the term "salt of said amino compound" is exemplified by organic acid salts such as formic, acetic, succinic, citric, lactic, maleic, fumaric, palmitic, cholic, pamoic, mucic, D-glutamic, d-camphoric, glutaric, glycolic, phthalic, tartaric, lauric, stearic, salicylic, methanesulfonic, benzenesulfonic, para-toluenesulfonic, sorbic, puric, benzoic, cinnamic and like organic salts. The term also encompasses inorganic acid salts such as hydrochloric, hydrobromic, hydroiodic, sulfuric, phosphoric and like inorganic salts.

The term "amino-protecting group" or the equivalent term "protected amino" as employed in the present specification refers to an amino group substituted with one of the commonly employed amino-blocking groups, such as the tert-butoxycarbonyl group (t-BOC), the benzyloxycarbonyl group, the 4-methoxybenzyloxycarbonyl group, the 4-nitrobenzyloxycarbonyl group, the 2,2,2-trichloroethoxycarbonyl group, or the 1-carbomethoxy-2-propenyl group formed with methylacetoacetate. Further examples of groups referred to by the above terms are described by J. W. Barton in "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. All that is further required of these groups is that one skilled in the art is able to substitute and remove them from the molecule without disrupting the remainder of the molecule. The preferred amino protecting group is the tert-butoxycarbonyl group.

As used in the instant specification, the term "$C_1$ to $C_4$ alkanoylamino" includes groups such as formylamino, acetylamino, and isobutyrylamino. The term "$C_1$ to $C_4$ alkylsulfonylamino" encompasses groups such as N-(methylsulfonylamino), N-(ethylsulfonylamino) and N-(butylsulfonylamino).

Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-isopropylphenyl, 4-ethylphenyl, 3-(n-propyl)phenyl and the like; a mono- or di(alkoxy)phenyl group for example, 2,6-dimethoxyphenyl, 4-methoxyphenyl, 3-ethoxyphenyl, 4-isopropoxyphenyl, 4-t-butoxyphenyl, 3-ethoxy-4-methoxyphenyl and the like; a 3- or 4-trifluoromethylphenyl, a mono- or dicarboxyphenyl or protected carboxyphenyl group such as 4-carboxyphenyl or 2,4-di(protected carboxy)phenyl, a mono- or di(hydroxy)methylphenyl or protected hydroxymethylphenyl such as 3-(protected hydroxymethyl)phenyl or 3,4-di(hydroxymethyl)phenyl, a mono- or di(aminomethyl)phenyl or protected aminomethylphenyl such as 2-(aminomethyl)phenyl or 2,4-(protected aminomethyl)phenyl, or mono- or di[N-(methylsulfonylamino)]phenyl such as 3-[N-(methylsulfonylamino)]phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and like disubstituted phenyl groups bearing different substituents.

The terms "halo" and "halogen" refer to fluoro, chloro, bromo, or iodo.

The terms "protected hydroxy" and "hydroxy-protecting group" refer to readily cleavable groups bonded to hydroxyl groups such as the formyl group, the chloroacetoxy group, the benzhydryl group, the trityl group, the p-nitrobenzyl group, the trimethylsilyl group and the like. Further examples of groups referred to by the above terms are described by C. B. Reese and E. Haslam in "Protective Groups in Organic Chemistry", J. G. W. McOmie, Ed., Plenum Press, New York, N.Y., 1973, Chapters 3 and 4, respectively, and T. W. Greene, "Protective Groups in Organic Synthesis", John Wiley and Sons, New York, N.Y., 1981, Chapters 2 and 3. The preferred hydroxy protecting group is the trityl group.

The hydroxy protecting groups referred to by the above terms are mainly employed to prevent hydroxy functions (other than the C-3 hydroxy function) of the starting materials cephalosporin from reacting with the DEAD, DIMAD or di-(iso-propyl)azodicarboxylate reagent and the acetylenic-alkylalcohol. Of course the protecting group itself should not react with these reagents, and furthermore should be readily removable after, for example, the DEAD or DIMAD reaction without disrupting the remainder of the molecule.

Illustrative of the acyl groups

wherein $R_5$ is an arylalkyl group of the formula

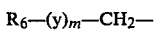

and m is zero are cyclohexa-1,4-dien-1-ylacetyl, phenylacetyl, 4-chlorophenylacetyl, 3-hydroxyphenylacetyl, 4-(protected hydroxy)phenylacetyl, 3-cyanophenylacetyl, 2-(aminomethyl)phenylacetyl, 4-hydroxy-3-methylphenylacetyl, 4-bromophenylacetyl, 4-ethoxyphenylacetyl, 4-nitrophenylacetyl, 4-carboxyphenylacetyl, 3,4-dimethoxyphenylacetyl, 2-(2-thienyl)acetyl, 3-(2-thienyl)acetyl, 2-(2-furyl)acetyl, 2-(1-tetrazolyl)acetyl, 2-(5-tetrazolyl)acetyl, 2-(2-thiazolyl)acetyl, 2-(2-aminothiazol-4-yl)acetyl, 2-(protected amino)thiazol-4-yl acetyl, and the like. In the above formula when m is one and y is an oxygen atom, representative acyl groups are phenoxyacetyl, 3-hydroxyphenoxyacetyl, 4-chlorophenoxyacetyl, 3,4-dichlorophenoxyacetyl, 2,4-dichlorophenoxyacetyl, 2-chlorophenoxyacetyl, 4-methoxyphenoxyacetyl, 2-ethoxyphenoxyacetyl, 3,4-dimethylphenoxyacetyl, 4-isopropylphenoxyacetyl, 3-cyanophenoxyacetyl, 3-nitrophenoxyacetyl, 4-(hydroxymethyl)phenoxy, 3-[N-(methylsulfonylamino)]phenoxyacetyl, 2-(aminomethyl)phenoxyacetyl, 3-(trifluoromethyl)phenoxyacetyl and like substituted groups. When m is one and y is a sulfur atom, representative groups of the above formula include phenylthioacetyl, 4-fluorophenylthioacetyl, 3-fluorophenylthioacetyl, 3-chlorophenylthioacetyl, 3,4-dichlorophenylthioacetyl, 2,5-dichlorophenylthioacetyl, 3-chloro-4-fluorophenylthioacetyl, 4-cyanophenylthioacetyl, 3-bromophenylthioacetyl, 4-(trifluoromethyl)-phenylthioacetyl, and like acyl groups.

Examples of $R_4$ when it is a group of the formula

wherein $R_5$ is a group of the formula

are the hydroxy-substituted arylalkyl groups such as the 2-hydroxy-2-phenylacetyl group of the formula

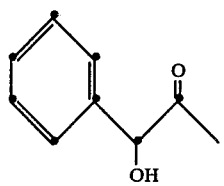

or the 2-formyloxy-phenylacetyl group of the formula

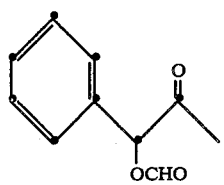

and similar groups wherein the phenyl ring is substituted and/or the hydroxy group is derivatized with a hydroxy protecting group, for example, 2-hydroxy-2-(4-methoxyphenyl)acetyl, 2-hydroxy-2-(3-chloro-4-hydroxyphenyl)acetyl, 2-formyloxy-2-(4-hydroxyphenyl)-acetyl, 2-hydroxy-2-(3-bromophenyl)acetyl, 2-formyloxy-2-(3,5-dichloro-4-hydroxyphenyl)acetyl, 2-formyloxy-2-(3-chloro-4-methoxyphenyl)acetyl, 2-hydroxy-2-(3-chlorophenyl)acetyl, 2-(protected hydroxy)-2-(phenyl)acetyl, 2-(protected hydroxy)-2-((4-protected hydroxy)phenyl)acetyl, and the like groups. Further examples when W is hydroxy, formyloxy or protected hydroxy are the heteroacetyl group such as the 2-hydroxy-2-(2-thienyl)acetyl, 2-formyloxy-2-(3- furyl)acetyl, 2-(protected hydroxy)-2-(1-tetrazolyl)acetyl, 2-hydroxy-2-(2-aminothiazol-4-yl)acetyl, 2-(protected hydroxy)-2-(2-(protected amino)thiazole-4-yl)acetyl and the like.

Representative of the above acyl groups when W is carboxy, protected carboxy or a carboxylate salt are 2-(carboxy)-2-phenylacetyl, 2-(t-butoxycarbonyl)-2-phenylacetyl, 2-(para-nitrobenzyloxycarbonyl)-2-phenylacetyl, 2-(diphenylmethoxycarbonyl)-2-phenylacetyl, 2-carboxy-2-(4-hydroxyphenyl)acetyl, 2-(t-butoxycarbonyl)-2-(4-hydroxyphenyl)acetyl, 2-paranitrobenzyloxycarbonyl)-2-(4-hydroxyphenyl)acetyl, 2-(diphenylmethoxycarbonyl)-2-(4-hydroxyphenyl)acetyl, 2-(carboxy)-2-(4-chlorophenyl)acetyl, 2-(carboxy)-2-(4-methoxyphenyl)acetyl, 2-(carboxy)-2-(3-nitrophenyl)acetyl, 2-carboxy-2-(2-thienyl)acetyl, 2-(allyloxycarbonyl)-2-(2-furyl)acetyl, 2-carboxy-2-(1-tetrazolyl)acetyl, 2-(t-butoxycarbonyl)-2-(5-tetrazolyl)acetyl, 2-carboxy-2-(2-thiazolyl)acetyl, 2-(para-nitrobenzyloxycarbonyl)-2-(2-aminothiazol-4-yl) and like groups, and when W is carboxy, and sodium and potassium salts thereof.

Examples of the above acyl groups when W is amino, a salt of said amino compound or a protected amino group, include 2-amino-2-phenylacetyl, 2-amino-2-(1,4-cyclohexadien-1-yl)acetyl, 2-(N-(t-butylcarbamato))-2-phenylacetyl), 2-amino-2-phenylacetyl hydrochloride, 2-amino-2-(4-hydroxyphenyl)acetyl, 2-(N-(t-butylcarbamato))-2-(4-hydroxyphenyl)acetyl, 2-(N-(t-butylcarbamato))-2-(4-trityloxyphenyl)acetyl, 2-amino-2-phenylacetyl hydrochloride, 2-amino-2-(3-(N-methylsulfonylamino)phenyl)acetyl, 2-(N-(t-butylcarbamato))-2-(3-(N-methylsulfonylamino)phenyl)acetyl, 2-amino-2-(2-thienyl)acetyl, 2-amino-2-(2-thienyl)acetyl hydrochloride, 2-amino-2-(3-thienyl)acetyl, 2-amino-2-(3-thienyl)acetyl hydrobromide, 2-amino-2-(2-furyl)acetyl, 2-amino-2-(2-furyl)acetyl sulfate, 2-amino-2-(3-furyl)acetyl, 2-(N-(t-butylcarbamato))-2-(3-furyl)acetyl, 2-amino-2-(1-tetrazolyl)acetyl, 2-(N-(allylcarbato))-2-(1-tetrazolyl)acetyl, 2-amino-2-(5-tetrazolyl)acetyl, 2-(N-(benzylcarbamato))-2-(5-tetrazolyl)acetyl, 2-amino-2-(2-thiazolyl)acetyl, 2-(N-(trimethylsilylamino))-2-(2-thiazolyl)acetyl, 2-amino-2-(2-aminothiazol-4-yl)acetyl, 2-(methyl N-(3-aminobut-2-enoate))-2-(2-aminothiazol-4-yl)acetyl, 2-amino-2-((2-protected amino)thiazol-4-yl)acetyl, 2-(N-(chloroacetamido))-2-((2-protected amino)thiazol-4-)acetyl, 2-amino-2-(benzothien-2-yl)acetyl, 2-amino-2-(benzothien-3-yl)acetyl, 2-(N-(t-butylcarbamato))-2-(benzothien-3-yl), 2-amino-2-(benzothien-3-yl)acetyl hydrochloride, 2-amino-2-(benzothien-2-yl)acetyl hydrochloride, 2-(N-(allylcarbamato))-2-(benzothien-2-yl)acetyl, 2-(N-(t-butylcarbamato)-2-(benzothien-2-yl)acetyl, 2-(N-(allylcarbamato))-2-(benzothien-3-yl)acetyl, 2-(N-(benzylcarbamato))-2-(5-hydroxybenzothien-3-yl)acetyl, 2-(N-(trimethylsilylamino))-2-(5-methoxybenzothien-3-yl)acetyl, 2-(N-(para-nitrobenzamido))-2-(6-fluorobenzothien-3-yl)acetyl, 2-(N-(2,2,2-trichloroethylcarbamato))-2-(4-fluorobenzothien-3-yl)acetyl, 2-(N-(2-chloroacetamido))-2-(5-fluorobenzothien-3-yl)acetyl, 2-amino-2-(7-fluorobenzothien-3-yl)acetyl, 2-amino-2-(6-methoxybenzothien-3-yl)acetyl sulfate, 2-(N-(t-butylcarbamato))-2-(5-chlorobenzothien-3-yl)acetyl, 2-(N-(allylcarbamato))-2-(6-chlorobenzothien-3-yl)acetyl, 2-(N-formamido)-2-(4,7-dichlorobenzothien-3-yl)acetyl, 2-(methyl N-(3-aminobut-2-enoate))-2-(5-bromo-2-methoxybenzothien-3-yl)acetyl, 2-amino-2-(6-hydroxybenzothien-3-yl)acetyl, 2-amino-2-(2-hydroxybenzothien-3-yl)acetyl hydrobromide, 2-(N-acetamido)-2-(6-ethoxy-2-methylbenzothien-3-yl)acetyl, 2-amino-2-(indol-2-yl)acetyl, 2-amino-2-(indol-3-yl)acetyl, 2-amino-2-(indol-2-yl)acetyl hydrochloride, 2-amino-2-(indol-3-yl)acetyl hydrochloride, 2-(N-(t-butylcarbamato))-2-(indol-2-yl)acetyl, 2-(N-(t-butylcarbamato))-2-(indol-3-yl)acetyl, 2-(N-(allylcarbamato))-2-(4-chloroindol-3-yl)acetyl, 2-amino-2-(2-hydroxyindol-3-yl)acetyl, 2-(N-(benzylcarbamato))-2-(7-methyl-4-bromoindol-3-yl)acetyl, 2-(N-(formamido))-2-(6-ethoxy-2-methylindol-3-yl)acetyl, 2-(N-trimethylsilylamino)-2-(5,6-difluoroindol-3-yl)acetyl, 2-(N-(2,2,2-trichloroethylcarbamato))-2-(6-nitroindol-3-yl)acetyl, 2-amino-(5-hydroxyindol-3-yl)acetyl hydrobromide, 2-amino-(6-hydroxyindol-3-yl)acetyl sulfate, 2-amino-2-(naphth-1-yl)acetyl, 2-amino-2-(naphth-2-yl)acetyl, 2-amino-2-(naphth-1-yl)acetyl hydrochloride, 2-amino-2-(naphth-2-yl)acetyl hydrochloride, 2-(N-(t-butylcarbamato))-2-(naphth-1-yl)acetyl, 2-(N-(t-butylcarbamato))-2-(naphth-2-yl)acetyl, 2-(N-(allylcarbamato))-2-(6-hydroxynaphth-2-yl)acetyl, 2-(N-(benzylcarbamato))-2-(6-methoxynaphth-2-yl)acetyl, 2-(N-formamido)-2-(6-chloronaphth-2-yl)acetyl, 2-(N-(2,2,2-trichloroethylcarbamato))-2-(8-nitronaphth-2-yl)acetyl, 2-amino-2-(5-nitronaphth-2-yl)acetyl sulfate, 2-amino-2-(8-methoxynaphth-2-yl)acetyl hydrobromide, 2-(N-(paranitrobenzamido))-2-(8-chloronaphth-2-yl)acetyl, 2-amino-2-(8-aminonaphth-2-yl)acetyl, 2-(N-(trimethylsilylamino))-2-(5-methoxy-1-chloronaphth-2-yl)acetyl, 2-(N-(t-butylcarbamato))-2-(7-ethyl-5-methylnaphth-2-yl)acetyl, 2-amino-2-(8-(n-propyl)-1-hydroxynaphth-2-yl)acetyl, and the like, and, when W is amino the zwitterion salt (in conjunction with the C-4 carboxy group) thereof.

When R$_4$ is a group of the formula

where in turn R$_5$ is a group of the formula

those skilled in the art will recognize that the carbon attached to both W and R$_7$ is asymmetric. The above formula for R$_5$ represents both the (R) and the (S) form, plus any percentage mixture of the two isomers. When W is amino, protected amino, a salt of said amino compound, hydroxy, protected hydroxy or formyloxy, the (R)-isomer of this carbon is preferred.

Examples of the substituent at C-3 of the cephalosporin in Formula 1, i.e. the substituent of the partial formula:

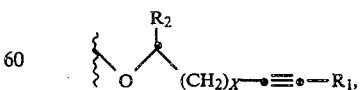

wherein R$_1$, R$_2$ and X are as defined for Formula 1, are as follows: (X is zero): prop-1-yn-3-yloxy, prop-1-yn-3-methyl-3-yloxy, prop-1-yn-3-benzyl-3-yloxy, but-2-yn-4-yloxy, hex-4-yn-6-ethyl-6-yloxy, prop-1-yn-1-(ethylsulfide)-3-yloxy, prop-1-yn-1-(phenylsulfide)-3-(phenethyl)-3-yloxy, methyl but-4-yloxy-2-ynoate, t-butyl but- 4-phenyl-4-yloxy-2-ynoate, prop-1-yn-1-chloro-3-yloxy, prop-1-yn-1-iodo-3-methyl-3-yloxy, (X is one) but-1-yn-4-yloxy, oct-5-yn-8-yloxy, but-1-yn-4-ethyl-4-yloxy, ethyl pent-5-yloxy-2-ynoate, isopropyl pent-5-yloxy-5-(phenethyl)-2-ynoate, but-1-(ethylsulfide)-1-yn-4-yloxy, but-1-(iso-butylsulfide)-1-yn-4-phenyl-4-yloxy, but-1-(phenylsulfide)-4-yloxy, but-1-(phenylsulfide)-4-benzyl-4-yloxy, but-1-fluoro-1-yn-4-yloxy, but-1-bromo-1-yn-4-phenyl-4-cyloxy, (X is 2) pent-1-yn-5-yloxy, hept-2-methyl-3-yn-7-yloxy, pent-1-yn-5-propyl-5-yloxy, methyl hex-6-yloxy-ynoate, isobutyl hex-6-ethyl-6-yloxy-2-ynoate, pent-1-yn-5-(methylsulfide)-1-yn-5-yloxy, pent-1-(n-propylsulfide)-5-(phenethyl)-5-yloxy, pent-1-(phenylsulfide)-1-yn-5-yloxy, pent-1-(phenylsulfide)-1-yn-5-methyl-5-yloxy, pent-1-bromo-1-yn-5-yloxy, pent-1-chloro-1-yn-5-benzyl-5-yloxy, (X is three), hex-1-yn-6-yloxy, oct-3-yn-6-yloxy, hex-1-yn-6-phenylyloxy, n-butyl hept-7-yloxy-2-ynoate, ethyl hept-7-benzyl-7-yloxy-2-ynoate, hex-1-(isopropylsulfide)-1-yn-6-yloxy, hex-1-(t-butylsulfide)-1-yn-6-ethyl-6-yloxy, hex-1-(phenylsulfide)-1-yn-6-yloxy, hex-1-(phenylsulfide)-1-yn-6-(isopropyl)-6-yloxy, hex-1-iodo-1-yn-6-yloxy, hex-1-fluoro-1-yn-6-(phenethyl)-6-yloxy, (X is four) hept-1-yn-7-yloxy, dec-4-yn-10-yloxy, hept-1-yn-7-(phenethyl)-7-yloxy, ethyl oct-8-yloxy-2-ynoate, n-propyl oct-8-phenyl-8-yloxy-2-ynoate, hept-1-(ethylsulfide)-1-yn-7-yloxy, hept-1-(n-butylsulfide)-1-yn-7-benzyl-7-yloxy, hept-1-(phenylsulfide)-1-yn-7-yloxy, hept-1-(phenylsulfide)-7-phenyl-7-yloxy, hept-1-bromo-1-yn-7-yloxy and hept-1-chloro-1-yn-7-propyl-7-yloxy.

In the formula and examples of the instant application, the carbon attached to the other oxygen is asymmetric when $R_2$ is other than hydrogen. Thus when $R_2$ is other than hydrogen the instant formulas and examples can represent either the pure S or pure R isomer or any mixture of the two.

One group of preferred compounds among those represented by Formula 1 above is where $R_4$ is hydrogen, which is the amino compound, and the salts of said amino compound. This group of preferred compounds is also called the "nucleus" compounds.

A preferred group of the above nucleus compounds is when X is zero, $R_2$ is hydrogen and $R_1$ is hydrogen, methyl, phenyl or methoxycarbonyl. A more preferred group within the preferred group is additionally when Z is hydrogen and $R_3$ is para-nitrobenzyl, benzhydryl, para-methoxybenzyl, hydrogen, a pharmaceutically-acceptable, non-toxic salt of the carboxy group or a hydrate of said salt. The most preferred nucleus compounds within the more preferred group are when $R_4$ is hydrogen or a hydrochloride salt or a paratoluenesulfonate salt of said compound.

Examples of this most preferred group of nucleus compounds include:
para-nitrobenzyl 7-(R)-amino-3-(prop-1'-yn-3'-yloxy)-3-cephem-4-carboxylate,
para-nitrobenzyl 7-(R)-amino-3-(prop-1'-yn-3'-yloxy)-3-cephem-4-carboxylate hydrochloride,
benzhydryl 7-(R)-amino-3-(prop-1'-yn-3'-yloxy)-3-cephem-4-carboxylate,
benzhydryl 7-(R)-amino-3-(prop-1'-yn-3'-yloxy)-3-cephem-4-carboxylate hydrochloride,
para-nitrobenzyl 7-(R)-amino-3-(but-2'-yn-4'-yloxy)-3-cephem-4-carboxylate,
para-nitrobenzyl 7-(R)-amino-3-(but-2'-yn-4'-yloxy)-3-cephem-4-carboxylate hydrochloride salt,
benzhydryl 7-(R)-amino-3-(1'-phenylprop-1'-yn-3'-yloxy)-3-cephem-4-carboxylate, and
para-nitrobenzyl 7-(R)-amino-3-(methyl but-4'-yloxy-2'-ynoate)-3-cephem-4-carboxylate hydrochloride salt.

A second group of preferred compounds within the group of above nucleus compounds occurs when X is from one to four, and especially when X is one, $R_2$ is hydrogen and $R_1$ is hydrogen, methyl, phenyl or methoxycarbonyl. A more preferred group within the preferred group is additionally when $R_3$ is para-nitrobenzyl, benzhydryl, para-methoxybenzyl, hydrogen, a pharmaceutically-acceptable, non-toxic salt of the carboxy group or a hydrate of said salt, and Z is hydrogen. The most preferred nucleus compounds within this more preferred group are when $R_4$ is hydrogen, a hydrochloride salt or a para-toluenesulfonate salt of said amino compound.

Examples of the second group of most preferred nucleus compounds include:
para-nitrobenzyl 7-(R)-amino-3-(but-1'-yn-4'-yloxy)-3-cephem-4-carboxylate,
benzhydryl 7-(R)-amino-3-(but-1'-yn-4'-yloxy)-3-cephem-4-carboxylate hydrochloride,
para-methoxybenzyl 7-(R)-amino-3-(pent-1'-yn-5'-yloxy)-3-cephem-4-carboxylate,
potassium 7-(R)-amino-3-(hex-1'-yn-6'-yloxy)-3-cephem-4-carboxylate hydrochloride, and
7-(R)-amino-3-(hept-1'-yn-7'-yloxy)-3-cephem-4-carboxylic acid.

A second group of preferred compounds among those represented by Formula 1 above are when $R_4$ is an amino-protecting group. This group of preferred compounds is also referred to as the "protected nucleus" compounds.

A preferred group of the above protected nucleus compounds occurs when X is zero, $R_2$ is hydrogen and $R_1$ is hydrogen, methyl, phenyl or methoxycarbonyl. A more preferred group within this preferred group is additionally when Z is hydrogen and $R_3$ is para-nitrobenzyl, benzhydryl, para-methoxybenzyl, hydrogen, a pharmaceutically-acceptable non-toxic salt of the carboxy group, or the hydrates of said salt. The most preferred protected nucleus compounds within the preferred group occurs when $R_4$ is t-butoxycarbonyl, benzyloxycarbonyl, 2,2,2-trichloroethoxycarbonyl, paramethoxycarbonyl, allyloxycarbonyl, trityl or trimethylsilyl.

Examples of this most preferred group of protected nucleus compounds include:
para-nitrobenzyl 7-(R)-(N-(t-butylcarbamato))-3-(prop-1'-yn-3'-yloxy)-3-cephem-4-carboxylate,
benzhydryl 7-(R)-(N-(allylcarbamato))-3-(prop-1'-yn-3'-yloxy)-3-cephem-4-carboxylate,
potassium 7-(R)-(N-(tritylamino))-3-(prop-1'-yn-3'-yloxy)-3-cephem-4-carboxylate,
para-methoxybenzyl 7-(R)-(N-(trimethylsilylamino))-3-(prop-1'-yn-3'-yloxy)-3-cephem-4-carboxylate and
7-(R)-(N-(benzylcarbamato))-3-(prop-1'-yn-3'-yloxy)-3-cephem-4-carboxylic acid.

A second preferred group of the above protected nucleus compounds occurs when X is from one to four, and especially when X is one, $R_2$ is hydrogen and $R_1$ is hydrogen, methyl, phenyl or methoxycarbonyl. A more preferred group within the preferred group occurs when additionally $R_3$ is para-nitrobenzyl, benzhydryl, para-methoxybenzyl, hydrogen, a pharmaceutically-acceptable, non-toxic salt of the carboxy group or the hydrates of said salt and Z is hydrogen. The most preferred compounds within this group of more preferred protected nucleus compounds is when R$_4$ is t-butoxycarbonyl, benzyloxycarbonyl, 2,2,2-trichloroethoxycarbonyl, para-methoxycarbonyl, trityl, allyloxycarbonyl, or trimethylsilyl.

Examples of the most preferred group of protected nucleus compounds include:
  para-nitrobenzyl 7-(R)-(N-(t-butylcarbamato))-3-(but-1'-yn-4'-yloxy)-3-cephem-4-carboxylate,
  benzhydryl 7-(R)-(N-(allylcarbamato))-3-(pent-1'-yn-5'-yloxy)-3-cephem-4-carboxylate,
  potassium 7-(R)-(N-(tritylamino))-3-(hex-1'-yn-6'-yloxy)-3-cephem-4-carboxylate,
  para-methoxybenzyl 7-(R)-(N-(trimethylsilylamino))-3-(hept-1'-yn-7'-yloxy)-3-cephem-4-carboxylate and
  7-(R)-(N-(benzylcarbamato))-3-(but-1'-yn-4'-yloxy)-3-cephem-4-carboxylate.

A third group of preferred compounds of Formula 1 occurs when R$_4$ is a group of the formula

This group of compounds is also called the "2-(aromatic)acetyl" group.

A preferred group of the 2-(aromatic)acetyl compounds occur when X is zero, R$_2$ is hydrogen, R$_1$ is hydrogen, methyl, phenyl or methoxycarbonyl and Z is hydrogen. A more preferred group within the preferred group is when m is zero, R$_6$ is phenyl, 2-thienyl, 3-thienyl, 2-furyl, 3-furyl, 1-tetrazolyl, 5-tetrazolyl, 2-thiazolyl, 2-aminothiazol-4-yl or 2-(protected amino)thiazol-4-yl, and R$_3$ is hydrogen, sodium ion, potassium ion, para-nitrobenzyl or benzhydryl.

Examples of this more preferred group of 2-(aromatic)acetyl compounds include:
  potassium 7-(R)-(phenylacetamido)-3-(prop-1'-yn-3'-yloxy)-3-cephem-4-carboxylate,
  sodium 7-(R)-(2-(fur-2-yl)acetamido)-3-(prop-1'-yn-3'-yloxy)-3-cephem-4-carboxylate,
  7-(R)-(2-(tetrazol-5-yl)acetamido)-3-(prop-1'-yn-3'-yloxy)-3-cephem-4-carboxylic acid,
  benzhydryl 7-(R)-(2-(tetrazol-1-yl)acetamido)-3-(prop-1'-yn-3'-yloxy)-3-cephem-4-carboxylate,
  para-nitrobenzyl 7-(R)-(2-(thiazol-2-yl)acetamido)-3-(prop-1'-yn-3'-yloxy)-3-cephem-4-carboxylate,
  Sodium 7-(R)-[2-(2-aminothiazol-4-yl)acetamido]-3-(prop-1'-yn-3'-yloxy)-3-cephem-4-carboxylate and
  para-nitrobenzyl 7-(R)-[2-(2-protected amino)thiazol-4-yl)acetamido]-3-(prop-1'-yn-3'-yloxy)-3-cephem-4-carboxylate.

A second more preferred group of compounds within the above preferred group of 2-(aromatic)acetyl compounds is when m is one and R$_3$ is hydrogen, sodium ion, potassium ion, para-nitrobenzyl or benzhydryl.

One group of most preferred compounds within the above group of more preferred compounds is when y is an oxygen atom and R$_6$ is phenyl. Examples of this group of most preferred compounds include:
  para-nitrobenzyl 7-(R)-(phenoxyacetamido)-3-(prop-1'-yn-3'-yloxy)-3-cephem-4-carboxylate,
  7-(R)-(phenoxyacetamido)-3-(prop-1'-yn-3'-yloxy)-3-cephem-4-carboxylic acid,
  para-nitrobenzyl 7-(R)-(phenoxyacetamido)-3-(1'-phenylprop-1'-yn-3'-yloxy)-3-cephem-4-carboxylate,
  7-(R)-(phenoxyacetamido)-3-(1'-phenylprop-1'-yn-3'-yloxy)-3-cephem-4-carboxylate,
  para-nitrobenzyl 7-(R)-(phenoxyacetamido)-3-(but-2'-yn-4'-yloxy)-3-cephem-4-carboxylate,
  7-(R)-(phenoxyacetamido)-3-(but-2'-yn-4'-yloxy)-3-cephem-4-carboxylic acid,
  para-nitrobenzyl 7-(R)-(phenoxyacetamido)-3-(methyl but-4'-yloxy-2'-ynoate)-3-cephem-4-carboxylate, and
  7-(R)-(phenoxyacetamido-3-(methyl but-4'-yloxy-2'-ynoate)-3-cephem-4-carboxylic acid.

A second group of most preferred compounds of the above group of more preferred compounds is when y is a sulfur atom and R$_6$ is phenyl, monofluorophenyl, 3-chlorophenyl, 3,4-dichlorophenyl, 3,5-dichlorophenyl or 2,5-dichlorophenyl. Examples of this group of most preferred copmounds include:
  7-(R)-(phenylthioacetamido)-3-(prop-1'-yn-3-yloxy)-3-cephem-4-carboxylate,
  para-nitrobenzyl 7-(R)-((2,5-dichlorophenylthio)acetamido)-3-(prop-1'-yn-3'-yloxy)-3-cephem-4-carboxylate,
  potassium 7-(R)-((3-fluorophenylthio)acetamido)-3-(but-2'-yn-4'-yloxy)-3-cephem-4-carboxylate,
  sodium 7-(R)((3-chlorophenylthio)acetamido)-3-(1'-phenylprop-1'-yn-3'-yloxy)-3-cephem-4-carboxylate,
  benzhydryl 7-(R)-((3,4-dichlorophenylthio)acetamido)-3-(methyl but-4'-yloxy-2'-ynoate)-3-cephem-4-carboxylate and
  7-(R)-((3,5-dichlorophenylthio)acetamido)-3-(but-2'-yn-4'-yloxy)-3-cephem-4-carboxylic acid.

A second preferred group of the 2-(aromatic)acetyl compounds occur when x is from one to four, and especially one, R$_1$ is hydrogen, methyl, phenyl or methoxycarbonyl and R$_2$ and Z are each hydrogen. One group of more preferred compounds within the second preferred group of compounds occurs when m is zero, R$_6$ is phenyl, 2-thienyl, 3-thienyl, 2-furyl, 3-furyl, 1-tetrazolyl, 5-tetrazolyl, 2-thiazolyl, 2-aminothiazol-4-yl or 2-(protected amino)thiazol-4-yl, and R$_3$ is hydrogen, sodium ion, potassium ion, para-nitrobenzyl or benzhydryl.

Examples of this more preferred group of 2-(aromatic)acetyl compounds include:
  potassium 7-(R)-(phenylacetamido)-3-(but-1'-yn-4'-yloxy)-3-cephem-4-carboxylate,
  sodium 7-(R)-(2-(fur-2-yl)acetamido)-3-(pent-1'-yn-5'-yloxy)-3-cephem-4-carboxylate,
  7-(R)-(2-(tetrazol-5-yl)acetamido)-3-(hex-1'-yn-6'-yloxy)-3-cephem-4-carboxylic acid,
  benzhydryl 7-(R)-(2-(tetrazol-1-yl)acetamido)-3-(hept-1'-yn-6'-yloxy)-3-cephem-4-carboxylate,
  para-nitrobenzyl 7-(R)-(2-(thiazol-2-yl)acetamido)-3-(but-1'-yn-4'-yloxy)-3-cephem-4-carboxylate,
  Sodium 7-(R)-[2-(2-aminothiazol-4-yl)acetamido]-3-(but-1'-yn-4'-yloxy)-3-cephem-4-carboxylate and
  para-nitrobenzyl 7-(R)-[2-(2-(protected amino)thiazol-4-yl)acetamido]-3-(pent-1'-yn-5'-yloxy)-3-cephem-4-carboxylate.

A second group of more preferred compounds within the second group of compounds occurs when m is one and R$_3$ is hydrogen, sodium, potassium, para-nitrobenzyl or benzhydryl. One group of most preferred compounds with the second group of more preferred compounds is when y is an oxygen atom and R₆ is phenyl, examples of which include:
- para-nitrobenzyl 7-(R)-(phenoxyacetamido)-3-(but-1'-yn-4'-yloxy)-3-cephem-4-carboxylate,
- 7-(R)-(phenoxyacetamido)-3-(but-1'-yn-4'-yloxy)-3-cephem-4-carboxylic acid,
- sodium 7-(R)-(phenoxyacetamido)-3-(but-1'-yn-4'-yloxy)-3-cephem-4-carboxylate,
- potassium 7-(R)-(phenoxyacetamido)-3-(pent-1'-yn-5'-yloxy)-3-cephem-4-carboxylate,
- benzhydryl 7-(R)-(phenoxyacetamido)-3-(1'-phenylpent-1'-yn-5'-yloxy)-3-cephem-4-carboxylate,
- 7-(R)-(phenoxyacetamido)-3-(hex-1'-yn-6'-yloxy)-3-cephem-4-carboxylate,
- para-nitrobenzyl 7-(R)-(phenoxyacetamido)-3-(methyl hept-7'-yloxy-2'-ynoate)-3-cephem-4-carboxylate and
- sodium 7-(R)-(phenoxyacetamido)-3-(hept-1'-yn-7'-yloxy)-3-cephem-4-carboxylate.

A second most preferred group of compounds wihtin the second group of more preferred compounds is when y is a sulfur atom and R₆ is phenyl, monofluorophenyl, 3-chlorophenyl, 3,4-dichlorophenyl, 3,5-dichlorophenyl or 2,5-dichlorophenyl. Examples of this group of most preferred compounds include:
- 7-(R)-(phenylthioacetamido)-3-(but-1'-yn-4'-yloxy)-3-cephem-4-carboxylate,
- para-nitrobenzyl 7-(R)-((2,5-dichlorophenylthio)acetamido)-3-(pent-1'-yn-5'-yloxy)-3-cephem-4-carboxylate,
- potassium 7-(R)-((3-fluorophenylthio)acetamido)-3-(hex-1'-yn-6'-yloxy)-3-cephem-4-carboxylate,
- sodium 7-(R)((3-chlorophenylthio)acetamido)-3-(hept-1'-yn-7'-yloxy)-3-cephem-4-carboxylate,
- benzhydryl 7-(R)-((3,4-dichlorophenylthio)acetamido)-3-(but-1'-yn-4'-yloxy)-3-cephem-4-carboxylate and
- 7-(R)-((3,5-dichlorophenylthio)acetamido)-3-(pent-2'-yn-5'-yloxy)-3-cephem-4-carboxylic acid.

A fourth group of preferred compounds among those represented by Formula 1 above is where R₄ is a group of the formula

wherein R₅ is a group of the formula

This group of preferred compounds is also called the "2-aromatic-2-(substituted)acetyl" group of compounds.

A preferred group of the 2-aromatic-2-(substituted)acetyl group of compounds is when X is zero and W is amino, a salt of said amino compound (including the zwitterion form) or a protected amino group and Z is hydrogen. A more preferred group within this preferred group of compound occurs when R₇ is phenyl, para-hydroxyphenyl, 2-benzothienyl, 3-benzothienyl, 2-indolyl, 3-indolyl, 2-naphthyl or 1-naphthyl, R₁ is hydrogen, methyl, phenyl or methoxycarbonyl and R₂ is hydrogen. An example of such compounds is 7-(R)-[2'-(R)-2'-(N-(t-butylcarbamato)-2'-phenylacetamido]-3-(prop-1'-yn-3'-yloxy)-3-cephem-4-carboxylate. The most preferred group of compounds is within the above group of more preferred compounds and occurs when W is amino or the hydrochloride salt of said amino compound, R₃ is hydrogen, and W is amino and taken in conjunction with R₃ form the zwitterion of said compound.

One favored group within the above most preferred group of compounds is when R₁ is hydrogen and R₇ is phenyl, para-hydroxyphenyl or 3-benzothienyl. Examples of this group include:
- 7-(R)-[2'-(R)-2'-amino-2'-phenylacetamido]-3-(prop-1'-yn-3'-yloxy)-3-cephem-4-carboxylic acid zwitterion,
- 7-(R)-[2'-(R)-2'-amino-2'-(para-hydroxyphenyl)acetamido]-3-(prop-1'-yn-3'-yloxy)-3-cephem-4-carboxylic acid zwitterion,
- 7-(R)-[2'-(R)-2'-amino-2'-(benzothien-3"-yl)acetamido]-3-(prop-1'-yn-3'-yloxy)-3-cephem-4-carboxylic acid zwitterion,
- 7-(R)-[2'-(R)-2'-amino-2'-phenylacetamido]-3-(prop-1'-yn-3'-yloxy)-3-cephem-4-carboxylic acid hydrochloride,
- 7-(R)-[2'-(R)-2'-amino-2'-(para-hydroxyphenyl)acetamido]-3-(prop-1'-yn-3'-yloxy)-3-cephem-4-carboxylic acid hydrochloride and
- 7-(R)-[2-(R)-2'-amino-2'-(benzothien-3"-yl)acetamido]-3-(prop-1'-yn-3'-yloxy)-3-cephem-4-carboxylic acid.

A second favored group within the above most favored group occurs when R₁ is methyl, phenyl or methoxycarbonyl and R₇ is phenyl. Examples of these favored compounds include:
- 7-(R)-[2'-(R)-2'-amino-2'-phenylacetamido]-3-(but-2'-yn-4'-yloxy)-3-cephem-4-carboxylic acid zwitterion,
- 7-(R)-[2'-(R)-2'-amino-2'-phenylacetamido]-3-(1'-phenylprop-3'-yloxy)-3-cephem-4-carboxylic acid zwitterion,
- 7-(R)-[2'-(R)-2'-amino-2'-phenylacetamido]-3-(methyl but-4'-yloxy-2'-ynoate)-3-cephem-4-carboxylic acid zwitterion,
- 7-(R)-[2'-(R)-2'-amino-2'-phenylacetamido]-3-(but-2'-yn-4'-yloxy)-3-cephem-4-carboxylic acid zwitterion,
- 7-(R)-[2'-(R)-2'-amino-2'-phenylacetamido]-3-(1'-phenylprop-1'-yn-3'-yloxy)-3-cephem-4-carboxylic acid hydrochloride and
- 7-(R)-[2'-(R)-2'-amino-2'-phenylacetamido]-3-(methyl but-4'-yloxy-2'-ynoate)-3-cephem-4-carboxylic acid hydrochloride.

A second group of most preferred compounds with above group of more preferred compounds occurs when W is protected amino, (especially when the amino group is protected with t-butoxycarbonyl, i.e. when W is a N-(t-butylcarbamato)group) and R₃ is benzhydryl or paranitrobenzyl. A favored group within the second group of most preferred compounds is when R₁ is hydrogen and R₇ is phenyl, para-hydroxyphenyl or 3-benzothienyl. Examples of such compounds include:
- Benzhydryl 7-(R)-[2'-(R)-2'-(N-(t-butylcarbamato))-2'-phenylacetamido]-3-(prop-1'-yn-3'-yloxy)-3-cephem-4-carboxylate,
- para-nitrobenzyl 7-(R)-[2'-(R)-2'-(N-(t-butylcarbamato))-2'-phenylacetamido]-3'-(prop-1'-yn-3'-yloxy)-3-cephem-4-carboxylate, benzhydryl 7-(R)-[2'-(R)-2'-(N-(t-butylcarbamato))-2'-(para-hydroxyphenyl)acetamido]-3'-(prop-1'-yn-3'-yloxy)-3-cephem-4-carboxylate, benzhydryl 7-(R)-[2'-(R)-2'-(N-(t-butylcarbamato))-2'-(benzothien-3"-yl)acetamido]-3-(prop-1'-yn-3'-yloxy)-3-cephem-4-carboxylate, para-nitrobenzyl 7-(R)-[2'-(R)-2'-(N-(t-butylcarbamato))-2'-(para-hydroxyphenyl)acetamido]-3'-(prop-1'-yn-3'-yloxy)-3-cephem-4-carboxylate and, para-nitrobenzyl 7-(R)-[2'-(R)-2'-(N-(t-butylcarbamato))-2'-(benzothien-3"-yl)acetamido]-3-(prop-1'-yn-3'-yloxy)-3-cephem-4-carboxylate.

A second preferred group within the above 2-aromatic-2-(substituted)acetyl group of compounds occurs when X is from one to four, and especially one, and W is amino, the salt of said amino compound (including the zwitterion form) or a protected amino group. A more preferred group of compounds within the above preferred group of compounds occurs when $R_7$ is phenyl, para-hydroxyphenyl, 1-naphthyl, 2-naphthyl, 2-indolyl, 3-indolyl, 2-benzothienyl or 3-benzothienyl, and $R_1$, $R_2$ and Z are each hydrogen.

One group of most preferred group of compounds within the more preferred group is when W is amino, the hydrochloride salt of said amino compound, $R_3$ is hydrogen, and when W is amino, $R_3$ and W together form the zwitterion of said compound. A favored group of compounds of this most preferred group occurs when $R_7$ is phenyl, para-hydroxyphenyl or 3-benzothienyl, examples of which include:

7-(R)-[2'-(R)-2'-amino-2'-phenylacetamido]-3-(but-1'-yn-4'-yloxy)-3-cephem-4-carboxylic acid zwitterion, 7-(R)-[2'-(R)-2'-amino-2'-(para-hydroxyphenyl)acetamido]-3-(but-1'-yn-4'-yloxy)-3-cephem-4-carboxylic acid zwitterion, 7-(R)-[2'-(R)-2'-amino-2'-(benzothien-3"-yl)acetamido]-3-(but-1'-yn-4'-yloxy)-3-cephem-4-carboxylic acid zwitterion, 7-(R)-[2'-(R)-2'-amino-2'-phenylacetamido]-3-(but-1'-yn-4'-yloxy)-3-cephem-4-carboxylic acid hydrochloride, 7-(R)-[2'-(R)-2'-amino-2'-(para-hydroxyphenyl)acetamido]-3-(but-1'-yn-4'-yloxy)-3-cephem-4-carboxylic acid hydrochloride and 7-(R)-[2'-(R)-2'-amino-2'-(benzothien-3"-yl)acetamido]-3-(but-1'-yn-4'-yloxy)-3-cephem-4-carboxylic acid hydrochloride.

A second group of most preferred compounds from the group of more preferred compounds occurs when W is a protected amino moiety, and especially when the protecting group is t-butoxycarbonyl (i.e., when W is (N-(t-butylcarbamato))). A favored group of compounds among this most preferred group is when $R_3$ is benzhydryl or para-nitrobenzyl and $R_7$ is phenyl, para-hydroxyphenyl or 3-benzothienyl. Examples of the favored group include:

benzhydryl 7-(R)-[2'-(R)-2'-(N-(t-butylcarbamato))-2'-phenylacetamido]-3-(but-1'-yn-4'-yloxy)-3-cephem-4-carboxylate, para-nitrobenzyl 7-(R)-[2'-(R)-2'-(N-(t-butylcarbamato))-2'-phenylacetamido]-3'-(but-1'-yn-4'-yloxy)-3-cephem-4-carboxylate, benzhydryl 7-(R)-[2'-(R)-2'-(N-(t-butylcarbamato))-2'-(para-hydroxyphenyl)acetamido]-3'-(but-1'-yn-4'-yloxy)-3-cephem-4-carboxylate, benzhydryl 7-(R)-[2'-(R)-2'-(N-(t-butylcarbamato))-2'-(benzothien-3"-yl)acetamido]-3-(but-1'-yn-4'-yloxy)-3-cephem-4-carboxylate, para-nitrobenzyl 7-(R)-[2'-(R)-2'-(N-(t-butylcarbamato))-2'-(para-hydroxyphenyl)acetamido]-3-(but-1'-yn-4'-yloxy)-3-cephem-4-carboxylate, and para-nitrobenzyl 7-(R)-[2'-(R)-2'-(N-(t-butylcarbamato))-2'-(benzothien-3"-yl)acetamido]-3-(but-1'-yn-4'-yloxy)-3-cephem-4-carboxylate.

The synthesis of the compounds of Formula 1 is represented in the following Scheme 1.

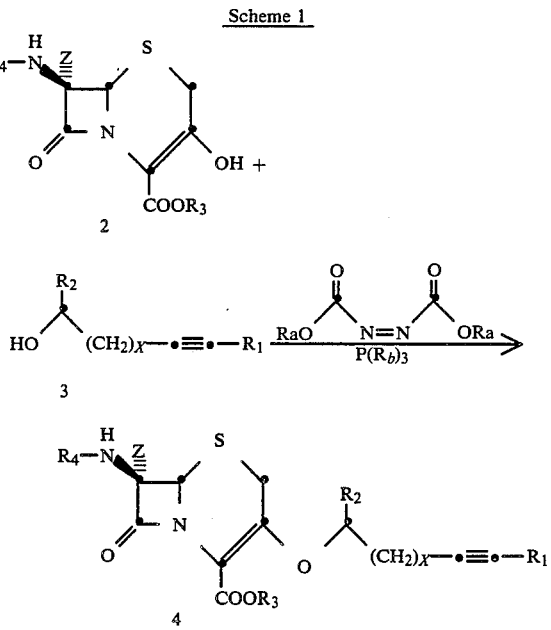

Scheme 1

In the above Scheme, $R_1$, $R_2$, $R_3$, $R_4$, X and Z have the same meaning as in Formula 1. $R_a$ is either methyl, giving dimethyl azodicarboxylate (DIMAD), ethyl, giving diethyl azodicarboxylate (DEAD) or iso-propyl giving di-(iso-propyl)azodicarboxylate.

Each $R_b$ in the above scheme is independently $C_1$ to $C_7$ alkyl, phenyl or phenyl substituted with $C_1$ to $C_4$ alkyl or $C_1$ to $C_4$ alkoxy. Examples of the phosphines that can be used in the process include alkyl phosphines such as trimethylphosphine, triethylphosphine, tripropylphosphine, tri(iso-propyl)phosphine, tributylphosphine, tri(tert-butyl)phosphine, tricyclohexylphosphine, tri(4-methylcyclohexyl)phosphine and the like; aryl phosphines such as triphenylphosphine, tri(p-tolyl)phosphine, tri(o-tolyl)phosphine, tri(m-tolyl)phosphine, tri(p-(n-propyl)phenyl)phosphine, tri(p-(tert-butyl)phenyl)phosphine, tri(p-methoxyphenyl)phosphine, tri(p-(isopropoxy)phenyl)phosphine, (o-methoxyphenyl)diphenylphosphine, (p-methoxyphenyl)diphenyl phosphine, and the like; and phosphines containing both alkyl and aryl groups, such as dimethylphenylphosphine, diphenylethylphosphine, di(p-methoxyphenyl)methylphosphine, di(p-tolyl)methylphosphine, (p-methoxyphenyl)phenylmethylphosphine, (p-tolyl)phenylmethylphosphine and the like. The preferred phosphine for use in the process is triphenylphosphine.

The stoichiometry of the process has the cephalosporin enol (or the corresponding acetic acid solvate), acetylenic alcohol, phosphine and alkyl azodicarboxylate reagent present in at least approximately a 1:1:1:1 molar ratio. The reaction will proceed in the presence of molar excesses above this ratio of any of the reagents or of the starting materials.

The process is initiated by first combining (in any order) the solvent, the cephalosporin enol (or the corresponding acetic acid solvate), the acetylenic alcohol and the phosphine, and secondly adding the azodicarboxylate reagent.

The reaction temperature of the process is a not critical parameter. The process can be carried out at a reaction temperature from approximately the freezing point to approximately the reflux temperature of the solvent. The preferred reaction temperature is approximately room temperature.

The duration of the process can be from approximately five minutes to approximately twenty four hours. The progress of the process can be monitored by standard methods (e.g., thin layer chromatography, high performance liquid chromatography, etc.) The process is stopped when the monitoring method demonstrates that the reaction is substantially complete.

The solvents for the instant process are aromatic hydrocarbon solvents such as benzene, toluene, xylenes, etc., ethers such as diethyl ether, tetrahydrofuran, 1,4-dioxane, chlorinated hydrocarbons such as methylene chloride, chloroform, carbon tetrachloride, dichloroethane, chlorobenzene, amides such dimethylformamide and dimethylacetamide and other solvents such as hexamethylphosphoramide. Tetrahydrofuran is the preferred solvent. It is also desirable, but not essential, to dry and deoxygenate the solvent before use in the process.

Hydroxy or carboxy groups on the substrate cephalosporin preferably should be protected before it is used in the instant process. However, the process will proceed when the carboxy and hydroxy groups of the cephalosporin are unprotected, with concomitant decrease in yields due to the alkylation of these unprotected groups.

The process is preferably carried out in an inert atmosphere.

The antibiotic compounds of Formula 1 are made in a variety of ways. One method is to simply acylate the 7β-amino, or "nucleus", compound with the appropriate 7-acyl side chain. The cephalosporin starting material for the acylation appears in Formula 1 when $R_4$ is hydrogen (i.e., the 7β-amino compound) or a salt of said 7β-amino compound. Alternatively, when $R_4$ is an amino-protecting group, the amino-protecting group is first removed to give the 7β-amino compound. The acylation conditions are similar to those used for 6-APA, 7-ADCA, 7-ACA and the like. Specifically, the free carboxylic acid form of the side chain or its acid salt can be combined with a condensing agent to acylate the 7β-amino nucleus. Suitable condensing agents include N,N'-disubstituted carbodiimides such as N,N'-dicyclohexylcarbodiimide, N,N'-diethylcarbodiimide, N,N'-di-(n-propyl)carbodiimide, N,N'-di-(isopropyl)-carbodiimide, N,N'-diallylcarbodiimide, N,N'-bis(p-dimethylaminophenyl)carbodiimide, N-ethyl-N'-(4"-ethylmorpholinyl)carbodiimide and the like, other suitable carbodiimides being disclosed by Sheehan in U.S. Pat. No. 2,938,892 and by Hofmann et al. U.S. Pat. No. 3,065,224; and azolides such as N,N'-carbonylimidazole, N,N'-thionyldiimidazol, etc. Also, dehydrating agents such as phosphorus oxychloride, alkoxyacetylenes, etc. and 2-halogenopyridinium salts (such as 2-chloropyridinium methyl iodide, 2-fluoropyridinium methyl iodide, etc.) may be used to couple the free acid or its acid salt with the 7β-amino nucleus.

Another acylation method entails first converting the free carboxylic acid form (or the corresponding salt) of the acyl side chain to the active ester derivative which is in turn used to acylate the nucleus. The active ester derivative is formed by esterifying the free acid form with groups such as p-nitrophenyl, 2,4-dinitrophenyl, trichlorophenyl, pentachlorophenyl, N-succinimide, N-maleic imide, N-phthalimide, vinyl, propargyl, cyanomethyl, methoxymethyl, pyranyl, pyridyl, piperidyl, 1H-benzotriazol-1-yl or 6-chloro-1H-benzotriazol-1-yl and also with groups that form mixed acid anhydrides, i.e. acylating the carboxylic acid of the acyl side chain with groups such as methoxycarbonyl, ethoxycarbonyl, iso-butoxycarbonyl, trichloromethylcarbonyl, and iso-but-2-ylcarbonyl.

Alternatively, the 7β-amino nucleus can be acylated with the N-ethoxycarbonyl-2-ethoxy-1,2-dihydroquinoline (EEDQ) derivative of the acyl side chain. In general, the free acid form of the acyl side chain and EEDQ are reacted in an inert, polar organic solvent (e.g. tetrahydrofuran, acetonitrile, etc.). The resultant EEDQ derivative is used in situ to acylate the 7β-amino nucleus. Procedures using an EEDQ ester for acylation are found in the Experimental Section.

Finally, when $R_4$ of the above Formula 1 is an acyl group of the formula

it is sometimes desirable to cleave the acyl group and replace it with another. The acyl side chain can be cleaved by standard methods. One such method uses phosphorus pentachloride and pyridine and is disclosed in B. Fechtig et al., U.S. Pat. No. 3,875,151, issued Apr. 1, 1975, herein incorporated by reference. Examples of this procedure can be found in the following Experimental Section. Another method uses a triphenylphosphite-chlorine kinetic complex and is described in Hatfield et al., U.S. Pat. No. 4,211,702 issued July 8, 1980.

Once the acyl side chain has been cleaved the resultant 7β-amino nucleus can be acylated with the desired acyl side using the various acylation procedures described above.

Deprotecting the amino, hydroxy and/or carboxy groups of these acylated compounds converts them to the antibiotic compounds encompassed by Formula 1. Of course, the hydroxy, amino and carboxy groups of the antibiotic compounds could also be in the form of pharmaceutically-acceptable salts, plus $R_3$ could be a non-toxic metabolically labile ester of the carboxy group.

The 3-hydroxy cephalosporin starting materials, depicted above in Scheme 1, are made by the following two methods. The first method converts a 3-chloro compound to the corresponding 3-hydroxy compound as depicted below in Scheme 2.

Scheme 2

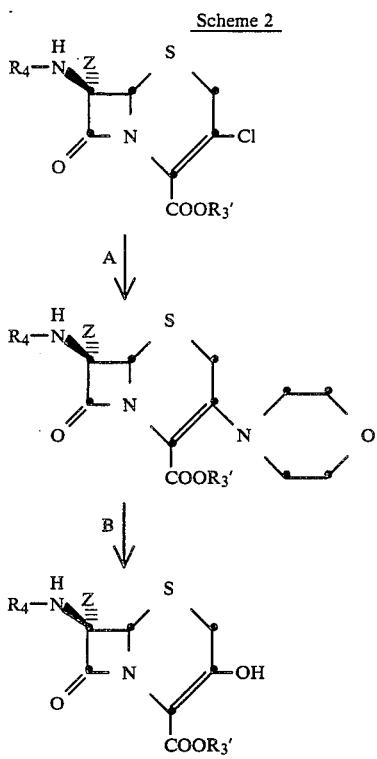

In the above Scheme 2, $R_4$ and Z are as defined for Formula 1, and $R_3'$ is a carboxy protecting group.

Step A in the above Scheme involves reacting the 3-chloro compound of formula 5 with morpholine in dimethylformamide. These conditions and equally suitable conditions are described in Spitzer, U.S. Pat. No. 4,013,651, issued Mar. 22, 1977, herein incorporated by reference.

The second method for making the 3-hydroxy starting materials, a 3-exomethylene cephalosporin compound of the formula 8

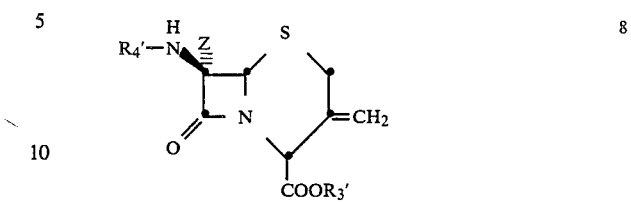

is reacted with ozone and the resultant intermediate is decomposed to give the corresponding 3-hydroxy starting material. In the above Formula 8, $R_4'$ is the same as $R_4$ for Formula 1 except that $R_4'$ should not be the free amine. $R_3'$ in Formula 8 is a carboxy protecting group inert to the conditions of the ozone reaction and the subsequent decomposition reaction.

In general, the 3-exomethylene compound of Formula 8 is dissolved in an inert organic solvent (e.g., ethyl acetate), the solution is cooled from between $-80°$ to $-50°$ C. and ozone is bubbled through the solution. Excess ozone is removed by bubbling either nitrogen or oxygen through the solution. The intermediate thus formed is then decomposed by passing gaseous sulfur dioxide through the stirred solution, (keeping the temperature of the solution from between $-80°$ C. to $0°$ C.) until aliquots of the solution test negative in the potassium iodide-starch test. The above conditions for converting a compound of the Formula 8 into the 3-hydroxy starting materials are further described in Chauvette, U.S. Pat. No. 3,917,587, issued Nov. 4, 1975, herein incorporated by reference.

Antibiotic activity of selected compounds of Formual 1 is illustrated by the following in vitro and in vivo test data in Table I, the minimum inhibitory concentration (MIC) for representative compounds against a wide range of gram-positive and gram-negative bacteria is presented. The MIC values were obtained by the standard agar dilution-method test.

TABLE 1

Antibiotic Activity of 3-alkynylalkyloxy cephalosporins
vs.
Gram-Positive and Gram-Negative Bacteria

| Test Organism* | Test Compound[1] Minimum Inhibitory Concentration (mcg/ml) | | | | | |
|---|---|---|---|---|---|---|
| | 1 | 2 | 3 | 4 | 5 | 6 |
| *Staphylococcus aureus* X1.1 | 2 | 2 | 8 | 1 | 1 | 0.5 |
| *Staphylococcus aureus* V41 | 32 | 128 | 128 | 8 | 8 | 64 |
| *Staphylococcus aureus* X400 | 64 | 128 | 128 | 64 | 32 | 64 |
| *Staphylococcus aureus* S13E | 32 | 128 | 128 | 16 | 8 | 64 |
| *Staphylococcus epidermidis* EPI1 | 8 | 32 | 128 | 8 | 8 | 16 |
| *Staphylococcus epidermidis* EPI2 | 2 | 2 | 8 | 1 | 2 | 1 |
| *Streptococcus pyogenes* C203 | 0.25 | 0.06 | 0.5 | 0.06 | 0.5 | 0.06 |
| *Streptococcus pneumoniae* Park I | 1 | 0.25 | 1 | 0.5 | 1 | 0.25 |
| Streptococcus group D X66 | 128 | 128 | 128 | 64 | 128 | 128 |
| Streptococcus group D 2041 | 128 | 64 | 128 | 32 | 2 | 32 |
| *Hemophilus influenzae* C.L. | 4 | 4 | 128 | 8 | 2 | 8 |
| *Hemophilus influenzae* 76 | 4 | 8 | 128 | 8 | 2 | 4 |
| *Escherichia coli* N10 | 4 | 16 | 128 | 4 | 128 | 8 |
| *Escherichia coli* EC14 | 2 | 4 | 64 | 2 | 64 | 4 |
| *Escherichia coli* TEM | 8 | 16 | 128 | 8 | 128 | 16 |
| *Klebsiella pneumoniae* X26 | 2 | 2 | 64 | 2 | 4 | 4 |
| *Klebsiella pneumoniae* KAE | 128 | 128 | 128 | 64 | 128 | 128 |

TABLE 1-continued

Antibiotic Activity of 3-alkynylalkyloxy cephalosporins vs. Gram-Positive and Gram-Negative Bacteria

| Test Organism* | Test Compound[1] Minimum Inhibitory Concentration (mcg/ml) | | | | | |
|---|---|---|---|---|---|---|
|  | 1 | 2 | 3 | 4 | 5 | 6 |
| *Klebsiella pneumoniae* X65 | 4 | 4 | 128 | 2 | 128 | 4 |

*Numerals and letters following the names of test microorganisms refer to the strains.
[1]Test compounds numbered 1-7 are as follows:
1 = 7-(R)-[2'-(R)-2'-amino-2'-phenylacetamido]-3-(prop-1'-yn-3'-yloxy)-3-cephem-4-carboxylic acid, zwitterionic form.
2 = 7-(R)-[2'-(R)-2'-amino-2'-phenylacetamido]-3-(but-2'-yn-4'-yloxy)-3-cephem-4-carboxylic acid, zwitterionic form.
3 = 7-(R)-[2'-(R)-2'-amino-2'-phenylacetamido]-3-(methylbut-4'-yloxy-2'-ynoate)-3-cephem-4-carboxylic acid, zwitterionic form.
4 = 7-(R)-[2'-(R)-2'-amino-2'-(para-hydroxyphenyl)acetamido]-3-(prop-1'-yn-3'-yloxy)-3-cephem-4-carboxylic acid, zwitterionic form.
5 = 7-(R)-[2'-(R)-2'-amino-2'-(benzothien-3"-yl)acetamido]-3-(prop-1'-yn-3'-yloxy)-3-cephem-4-carboxylic acid, zwitterionic form.
6 = 7(R)-(2'-(R)-2'-amino-2'-phenylacetamido]-3-(but-1'-yn-4'-yloxy)-3-cephem-4-carboxylic acid, zwitterionic form.

One antibiotic compound of Formula 1 i.e. 7-(R)-[2'-(R)-2-amino-2-phenylacetamido]-3-(prop-1'-yn-3'-yloxy)-3-cephem-4-carboxylic acid ("3-propargyloxy compound"), has demonstrated excellent oral absorption characteristics in mice and high plasma levels in rats in preliminary tests. The in vivo test results from mice and rats for the 3-proparglyoxy compound is set forth below in Table 2 and 3. The comparison compound in the following tables is cephalexin monohydrate ("3-methyl compound").

Table 2 below sets forth the plasma levels in mice orally dosed at 20 mg/kg of the 3-propargyloxy compound and the 3-methyl compound. The values for the 3-propargyloxy compound are average values computed from two animals at each time point while the values reported for the 3-methyl compound are average values from four or more animals at each time point.

TABLE 2

| Compound | Mouse Plasma Levels (μg/ml) Time From Dose (minutes) | | | |
|---|---|---|---|---|
|  | 20 | 40 | 60 | 120 |
| 3-propargyloxy | 23.1 | 12.4 | 4.0 | 0.85 |
| 3-methyl | 23.5 | 10.5 | 5.2 | 1.0 |

Table 3 gives data obtained from similar tests using rats. Rats were orally dosed with 20 mg/kg of the 3-propargyloxy compound (two rats) and the 3-methyl compound (four rats). The values reported in the Table are averaged values.

TABLE 3

| Compound | Rat Plasma Levels (μg/ml) Time From Dose (minutes) | | | | | |
|---|---|---|---|---|---|---|
|  | 20 | 60 | 120 | 240 | 360 | 540 |
| 3-propargyloxy | 3.9 | 15.9 | 19.3 | 14.7 | 12.3 | 8.5 |
| 3-methyl | 2.8 | 5.7 | 6.0 | 5.2 | 3.2 | 1.1 |

The antibiotic compounds of this invention are useful for the therapeutic or prophylactic treatment of infections in warm-blooded animals caused by both gram-positive and gram-negative organisms. For example, such antibiotics are useful for treating infections of farm animals such as colibacillosis. Alternatively, the compounds can be used as surface disinfectants.

The antibiotic can be administered orally, parenterally (e.g. intravenously, intramuscularly, subcutaneously, etc.) or as a topical ointment in treating bacterial infections of warm-blooded animals. The instant antibiotic compounds are preferably administered orally.

A further aspect of this invention is the pharmaceutical compositions of the antibiotics compounds of Formula 1. In particular, these pharmaceutical compositions are useful for the control of gram-positive bacterial infections and comprise a suitable vehicle and an antibacterially effective amount of the compound of Formula 1, wherein:

$R_3$ is hydrogen, a pharmaceutically-acceptable, non-toxic salt of the carboxy group, a hydrate of said salt, or a non-toxic, metabolically-labile ester of the carboxy group;

$R_4$ is a group of the formula:

wherein $R_5$ is
(i) 1,4-cyclohexadienyl, 1-cyclohexenyl, phenyl or substituted phenyl wherein the substituents are 1 or 2 halogens, hydroxy, nitro, cyano, trifluoromethyl, $C_1$ to $C_4$ alkyl, $C_1$ to $C_4$ alkoxy, carboxy, carboxymethyl, hydroxymethyl, aminomethyl, or N-(methylsulfonylamino);
(ii) an arylalkyl group of the formula

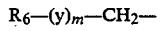

wherein y is O or S, m is 0 or 1, $R_6$ is $R_5$ as defined above, and when m is 0, $R_6$ is also 2-thienyl, 3-thienyl, 2-furyl, 3-furyl, 1-tetrazol, 5-tetrazol, 2-thiazolyl, or 2-aminothiazol-4-yl; or
(iii) a substituted arylalkyl group of the formula

wherein
$R_7$ is $R_6$ as defined above, 2- or 3-indolyl, substituted 2- or 3-indolyl of the formula

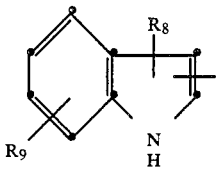

in which

R$_8$ and R$_9$ independently are hydrogen, halo, hydroxy, C$_1$ to C$_4$ alkyl, C$_1$ to C$_4$ alkoxy, nitro, amino, C$_1$ to C$_4$ alkanoylamino, C$_1$ to C$_4$ alkylsulfonylamino, or when R$_8$ and R$_9$ are on adjacent carbons, they may be taken together to form methylenedioxy; 2- or 3-benzothienyl, 2- or 3-substituted benzothienyl of the formula

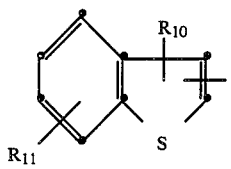

in which

R$_{10}$ and R$_{11}$ are independently hydrogen, halo, hydroxy, C$_1$ to C$_4$ alkyl, C$_1$ to C$_4$ alkoxy, nitro, amino, C$_1$ to C$_4$ alkanoylamino, C$_1$ to C$_4$ alkylsulfonylamino, and when R$_{10}$ and R$_{11}$ are on adjacent carbon atoms, they can be taken together to form methylenedioxy; 1- or 2-naphthyl, substituted 1- or 2-naphthyl of the formula

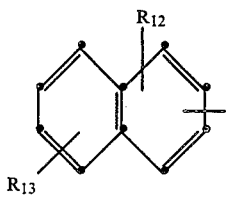

wherein

R$_{12}$ and R$_{13}$ are independently hydrogen, halo, hydroxy, C$_1$ to C$_4$ alkyl, C$_1$ to C$_4$ alkoxy, nitro, amino, C$_1$ to C$_4$ alkanoylamino, C$_1$ to C$_4$ alkylsulfonylamino, or when R$_{12}$ and R$_{13}$ are on adjacent carbon atoms, they can be taken together to form methylenedioxy; and W is hydroxy, formyloxy, carboxy, a carboxy salt, amino, or a salt of said amino compound provided that, when W is other than amino or a salt of said amino compound, R$_7$ is other than 2 or 3-indolyl, substituted 2- or 3-indolyl, 2- or 3-benzothienyl, 2- or 3-substituted benzothienyl, 1- or 2-naphthyl, or substituted 1- or 2-naphthyl; and wherein X is 0 to 4 and Z is hydrogen or methoxy.

Most of the above terms are as described for Formula 1. With regard to compositions for oral administration to warm blooded animals (e.g. tablets and capsules), the term "suitable vehicle" means common excipients such as binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; disintegrators such as croscarmellose sodium, microcrystalline cellulose, corn starch, sodium starch glycolate, alginic acid and mutable wetting agents such as sodium lauryl sulfate; and lubricants such as magnesium stearate and other metallic stearates, stearic acid, silicone fluid, talc, waxes oils and colloidal silica. Flavoring agents such as peppermint, oil of wintergreen, cherry flavoring or the like can also be used. It may be desirable to add a coloring agent to make the dosage form more aesthetically pleasing in appearance or to help identify the product. The tablets may also be coated by methods well known in the art.

When used in conjunction with oral liquid preparations, which may be aqueous or oily suspensions, solutions, emulsions or syrups; or a dry powder to be reconstituted before use with water or other suitable vehicles, the term "suitable vehicle" means conventional additives such as suspending agents, e.g., sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol or ethyl alcohol; and preservatives such as methyl or propyl p-hydroxybenzoates or sorbic acid.

The pharmaceutical composition can also be for intravenous (IV) use. Specifically, a water soluble form of the antibiotic can be dissolved in one of the commonly used intravenous fluids and administered by infusion. When used in conjunction with compositions for IV use, the term "suitable vehicle" means such fluids as physiological saline, Ringer's solution or 5% dextrose solution.

The pharmaceutical compositions can be for intramuscular preparations. A sterile formulation of a suitable salt form of the antibiotics of the instant invention, for example the hydrochloride salt, can be formulated with a "suitable vehicle", e.g., in a pharmaceutical diluent such as Water-for-Injection, physiological saline, 5% glucose or as a suspension in an aqueous base or a pharmaceutically acceptable oil base, e.g. an ester of a long chain fatty acid such as ethyl oleate.

Topical applications of the instant antibiotic compounds, are another form of the present pharmaceutical composition. The topical compositions can be formulated with "suitable vehicles" such as hydrophobic or hydrophillic bases which include ointments, creams or lotions.

For veterinary pharmaceutical compositions the instant antibiotic compounds may be administered in the feed or the drinking water of farm animals. Alternatively, the compounds can be formulated as intramammary preparations with "suitable vehicles" such as long- or quick-release bases.

Alternatively, the unit dosage form of the antibiotic can be a solution of the antibiotic or preferably a salt thereof in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

The term "antibacterially effective amount" means from approximately 0.5 to about 600 mg/kg of the antibiotic compound. This amount generally runs from about 250 mg to about 1.0 g per day for an adult human.

A preferred pharmaceutical composition occurs when, in the above pharmaceutical composition: R$_3$ is hydrogen, sodium cation or potassium cation, R₄ is a group of the formula:

wherein R₅ is a group of the formula

and R₇ is phenyl, para-hydroxyphenyl or 3-benzothienyl and W is amino or a salt of said amino compound, or when W is amino and R₃ is hydrogen they are taken in conjunction to form the zwitterion, and Z is hydrogen.

In a further aspect, this invention provides a method for treating or controlling infectious diseases, especially those caused by gram-positive microorganisms, in warm-blooded animals. This method comprises administering to the animal an effective dose of an instant antibiotic compound. An effective dose is generally between about 0.5 and about 600 mg/kg of the antibiotic compound. A typical daily dose for an adult human is from about 250 mg to about 1.0 g.

In practicing this method, the antibiotic can be administered in a single daily dose or in multiple doses per day. The treatment regime may require administration over extended periods of time, e.g., for several days or for from two or three weeks. The amount per administered dose or the total amount administered will depend on such factors as the nature and severity of the infection, the age and general health of the patient, the tolerance of the patient to the antibiotic and the microorganism or microorganisms involved in the infection.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg to about 1500 mg of the active ingredient; however, in general, it is preferably to employ a dosage amount in the range of from about 100 mg to 1000 mg. In parenteral administration the unit dosage is usually the pure compound in a slightly acidified sterile water solution or in the form of a soluble powder intended for solution.

The following Examples are provided to further illustrate the invention. It is not intended that the invention be limited in scope by reason of any of the following Preparations or Examples.

In the following Preparations and Examples, the terms nuclear magnetic resonance spectra, field desorption mass spectra, fast atom bombardment mass spectra infra-red spectra, ultraviolet spectra, elemental analysis, high performance and liquid chromatography are abbreviated n.m.r., f.d.m.s., f.a.b.m.s., i.r., u.v., anal. and HPLC, respectively. In addition, the adsorption maxima listed for the i.r. spectra are only those of interest and not all of the maxima observed.

The abbreviations THF, DEAD and DIMAD stand for tetrahydrofuran, diethyl azodicarboxylate and dimethyl azodicarboxylate, respectively.

In conjunction with the n.m.r. spectra, the following abbreviations are used: "s" is singlet, "d" is doublet, "dd" is doublet of doublets, "br. s" is broad singlet, "t" is triplet, "q" is quartet, "m" is multiplet. "J" indicates the coupling constant in Hertz. "DMSO/d₆" is dimethyl sulfoxide where all protons have been replaced with deuterium.

The n.m.r. spectra were obtained on a Varian Associates EM-390 90 MHz or T-60 instrument, or on a Jeol FX-90 90 MHz instrument. The chemical shifts are expressed in δ values (parts per million downfield from tetramethylsilane). The field desorption mass spectra were taken on a Varian-MAT 731 Spectrometer using carbon dendrite emitters. Infrared spectra were obtained on a Perkin-Elmer 281 instrument. Ultraviolet Spectra were obtained on a Cary 118 instrument. Thin layer chromatography was carried out on E. Merck silica gel plates.

EXPERIMENTAL SECTION

Example 1

Para-nitrobenzyl 7-(R)-phenoxyacetamido-3-(prop-1'-yn-3'-yloxy)-3-cephem-4-carboxylate Procedure A Para-nitrobenzyl 7-(R)-phenoxyacetamido-3-hydroxy-3-cephem-4-carboxylate (0.300 g, $6.18 \times 10^{-4}$M), triphenylphosphine (0.203 g, $7.72 \times 10^{-4}$M) and tetrahydrofuran (10 ml, dried, degassed) were combined under an argon atmosphere. A THF solution (approx. 5 ml) of propargyl alcohol (0.045 ml, $7.72 \times 10^{-4}$M) then a THF solution (approx. 5 ml) of DEAD (0.12 ml, $7.72 \times 10^{-4}$M) was added to the solution. The solution was stirred at room temperature for 18 hours then evaporated to a froth at 55° C. The froth was chromatographed on silica gel (8.0 g, E. Merck, packed with toluene) using a gradient of toluene (400 ml) versus 40% ethylacetate/toluene (400 ml). The product-containing fractions were combined and evaporated in vacuo. Diethyl ether was added to the residue and the solution was stirred at 55° C. then decanted to yield 89 mg of para-nitrobenzyl 7-(R)-phenoxyacetamido-3-(prop-1'-yn-3'-yloxy)-3-cephem-4-carboxylate contaminated with some diethyl hydrazino carboxylate.

Procedure B

Para-nitrobenzyl 7-(R)-phenoxyacetamido-3-hydroxy-3-cephem-4-carboxylate acetic acid solvate (5.455 g, $1.0 \times 10^{-2}$M) was dissolved in dried tetrahydrofuran (50 ml), then triphenylphosphine (2.885, $1.1 \times 10^{-2}$M) was added. A tetrahydrofuran solution (25 ml) of propargyl alcohol (0.617 g, $1.1 \times 10^{-2}$M) was added to the stirred solution with a tetrahydrofuran wash. Finally, DIMAD (1.607 g, $1.1 \times^{-2}$M) was added to the stirred solution with a tetrahydrofuran wash. The solution was stirred for 25 minutes at room temperature then evaporated to an oil at 35° C. The residue was taken up in ethyl acetate (approx. 30 ml), washed with water (4x), aqueous soidum chloride solution (1x), dried over sodium sulfate, filtered and evaporated to dryness to give the crude product.

The crude product was purified with HPLC (silica gel column, gradient of hexane versus 40% ethyl acetate/hexane then 40% ethyl acetate/hexane versus 50% ethyl acetate/hexane at a flow rate of 250 ml/min) to give 3.098 g, 59.2% yield of para-nitrobenzyl 7-(R)- phenoxyacetamido-3-(prop-1'-yn-3'-yloxy)-3-cephem-4-carboxylate: n.m.r. (60 MHz, CDCl$_3$) δ2.67 (m, J=2, 1, acetylenic proton), 3.53 (s, 2, C-2 protons), 4.58 (s, 2, methylene protons of phenoxyacetamido group, 4.70 (d, J=2, 2, methylene protons of propargyloxy group), 5.03 (d, J=4, 1, C-6 proton), 5.32 (m, 2, methylene protons of para-nitrobenzyl group), 5.67 (dd, J=1, 1, C-7 proton); f.d.m.s.: M=523; i.r. (CHCl$_3$): 3290, 2130, 1780 cm$^{-1}$.

Example 2

Benzhydryl 7-(R)-[(2'R)-2'-(N-(t-butylcarbamato))-2'-phenylacetamido]-3-(prop-1'-yn-3'-xyoly)-3-cephem-4-carboxylate Under an argon atmosphere, benzhydryl 7-(R)-[(2'R)-2'-(N-(t-butylcarbamato))-2'-phenylacetamido]-3-hydroxy-3-cephem-4-carboxylate (1.133 g, 1.38×10$^{-3}$M) and triphenylphosphine (0.362 g, 1.38×10$^{-3}$M) were dissolved in dried tetrahydrofuran (approx. 20 ml). Propargyl alcohol (0.08 ml, 1.38×10$^{-3}$M) was added then DIMAD (0.202 g, 1.38×10$^{-3}$M) was washed into the solution with THF. The solution was stirred for 45 minutes at room temperature. The solution was washed with water (4X), aqueous sodium chloride solution (1X), dried over sodium sulfate, filtered and evaporated to dryness. The residue was combined with the residue from a repitition of the above conditions (on a 1.62×10$^{-4}$M scale) and chromatographed on silica gel (8 g, packed with toluene), using a gradient elution of toluene (500 ml) versus 1:1 ethylacetate:toluene (500 ml) to yield 7.12 mg of benzhydryl 7-(R)-[(2'R)-2'-(N-(t-butylcarbamato))-2'-phenylacetamido]-3-(prop-1'-yn-3'-yloxy)-3-cephem-4-carboxylate: n.m.r. (90 MHz, CDCl$_3$): δ1.4 (s, 9, t-butyl group protons), 2.5 (m, 1, acetylenic proton), 3.1 (m, 2, C-2 proton), 4.4 (m, 2, methylene protons of propargyloxy group), 4.9 (d, J=4, 1, C-6 proton), 5.2 (d, J=6, 1, proton on carbamato group nitrogen), 5.6 (dd, J=4,8, 1, C-7 proton), 5.76 (d, J=6,1, methine proton of phenylacetamido group); i.r. (CHCl$_3$): 3300, 1778 cm$^{-1}$.

Example 3

Para-nitrobenzyl 7-(R)-[(2'R)-2'-(N-(t-butylcarbamato))-2'-phenylacetamido]-3-(prop-1'-yn-3'-yloxy)-3-cephem-4-carboxylate Under an argon atmosphere, para-nitrobenzyl 7-(R)-amino-3-(prop-1'-yn-3'-yloxy)-3-cephem-4-carboxylate (1.406 g, 3.60×10$^{-3}$M) was dissolved in dried tetrahydrofuran (approx. 10 ml). N-ethoxycarbonyl-2-ethoxy-1,2-dihydroquinoline (EEDQ, 0.908 g, 3.67×10$^{-3}$M) and 2-(R)-2-(N-(t-butylcarbamato))-2-phenylacetic acid (0.923 g, 3.67×10$^{-3}$M) were washed into the solution with THF. The reaction mixture was stirred at room temperature for 16 hours. The mixture was washed with water (1X), aqueous sodium bicarbonate solution (1X), 1N hydrochloric acid (1X), aqueous sodium chloride solution (1X), dried over sodium sulfate, filtered and evaporated to dryness. The residue was chromatographed on silica gel (15 g, packed with toluene) using a gradient elution of toluene (600 ml) versus 1:1 ethyl acetate:toluene (600 ml) to give 1.260 g, 56% yield of paranitrobenzyl 7-(R)-[(2'R)-2'-(N-(t-butylcarbamato))-2'-phenylacetamido]-3-(prop-1'-yn-3'-yloxy)-3-cephem-4-carboxylate: n.m.r. (90 MHz, CDCl$_3$): δ1.4 (s, 9, t-butyl-group, protons), 2.6 (m, 1, acetylenic proton), 4.6 (d, J=2,2, methylene protons of propargyloxy group), 4.9 (d, J=4, 1, C-6 proton), 5.2 (m, 3, methylene protons of p-nitrobenzyl group and methine proton of phenylacetamido group), 5.6 (m, 2, C-7 proton and proton on nitrogen of carbamato group), 6.8 (d, J=7, 1, proton on nitrogen of carbamato group); f.d.m.s.: M=623; i.r. (CHCl$_3$): 3300, 2135, 1780 cm$^{-1}$.

Example 4

Benzhydryl 7-(R)-[(2'R)-2'-(N-(t-butylcarbamato))-2'-(para-hydroxyphenyl)acetamido]-3-(prop-1'-yn-3'-yloxy)-3-cephem-4-carboxylate Under an argon atmosphere, benzhydryl 7-(R)-amino-3-(prop-1'-yn-3'-yloxy)-3-cephem-4-carboxylate (0.380 g, 9.04×10$^{-4}$M) was dissolved in dried tetrahydrofuran (approx. 5 ml). (2R)-2-(N-(t-butylcarbamato))-2-(para-hydroxyphenyl)acetic acid (0.246 g, 9.22×10$^{-4}$M) and N-ethoxycarbonyl-2-ethoxy-1,2-dihydroquinoline (EEDQ, 0.228 g, 9.22×10$^{-4}$M) were washed into the solution with THF the resultant solution was stirred at room temperature for 18 hours. The solution was washed with water (1X), aqueous sodium bicarbonate solution (1X), 1N hydrochloric acid (1X), sodium chloride solution, dried over sodium sulfate, filtered and evaporated to dryness. The residue from this procedure was combined with the residue from a repetition of the above procedure, chromatographed on silica gel (8 g, packed in toluene) with a gradient elution of toluene (500 ml) versus 80% ethyl acetate/toluene (500 ml) to yield 777 mg of benzhydryl 7-(R)-[(2'R)-2'-(N-(t-butylcarbamato))-2'-(para-hydroxyphenyl)acetamido]-3-(prop-1'-yn-3'-yloxy)-3-cephem-4-carboxylate: n.m.r. (90 MHz, CDCl$_3$): δ2.4 (s, t-butyl protons), 2.5 (m, acetylenic proton), 3.2 (s, C-2 protons), 4.4 (s, methylene protons of propargyloxy group), 4.8 (d, J=4, C-6 proton), 5.1 (d, J=5, methine proton of p-hydroxyphenylacetamido group), 5.5 (dd, J=4, 7, C-7 proton), 5.7 (d, J=5, proton on nitrogen of carbamato group); i.r. (CHCl$_3$): 1775 cm$^{-1}$; f.d.m.s.: M=670.

Example 5

Benzhydryl 7-(R)-[(2'R)-2'-(N-(t-butylcarbamato))-2'-(benzothien-3''-yl)acetamido]-3-(prop-1'-yn-3'-oxy)-3-cephem-4-carboxylate Under an argon atmosphere, benzhydryl 7-(R)-[(2'R)-2'-(N-(t-butylcarbamato))-benzothien-3''-yl)-acetamido]-3-hydroxy-3-cephem-4-carboxylate (0.693 g, 1.03×10$^{-3}$M) was dissolved in dried tetrahydrofuran (approx. 20 ml) then triphenylphosphine (0.271 g, 1.03×10$^{-3}$M) and propargyl alcohol (0.06 ml, 1.03×10$^{-3}$M) were added. DIMAD (0.151 g, 1.03×10$^{-3}$M), was washed into the solution. The solution was stirred at room temperature for 20 minutes then washed with water (4X), aqueous sodium chloride solution (1X), dried over sodium sulfate, filtered and evaporated to dryness. The resultant white foam was chromatographed on silica gel (8 g, packed in toluene) eluting with 10% ethyl acetate/toluene (700 ml) to yield 382 mg, 52% yield of benzhydryl 7-(R)-[(2'R)-2'-(N-(t-butylcarbamato))-2'-(benzothien-3''-yl)acetamido]-3-(prop-1'-yn-3'-yloxy)-3-cephem-4-carboxylate: n.m.r. (90 MHz, CDCl$_3$): δ1.36 (s, 9, t-butyl group protons), 2.48 (m, 1, acetylenic proton), 3.08 (s, 2, C-2 proton), 4.40 (m, 2, methylene protons of propargyloxy group), 4.88 (d, J=4, 1, C-6 proton), 5.6 (M, 3, C-7 proton and methine proton of benzothien-3'-ylacetamido group); f.d.m.s.: M=709.

Example 6

Para-nitrobenzyl 7-(R)-phenoxyacetamido-3-(but-2'-yn-4'-yloxy)-3-cephem-4-carboxylate

Under an argon atmosphere, para-nitrobenzyl 7-(R)-phenoxyacetamido-3-hydroxy-3-cephem-4-carboxylate (4.000 g, $7.33 \times 10^{-3}$M) was dissolved in dried tetrahydrofuran (50 ml). Triphenylphosphine (2.116 g, $8.07 \times 10^{-3}$M) was dissolved in the solution then a THF solution (40 ml) of but-2-yn-4-ylol (0.565 g, $8.07 \times 10^{-3}$M) ml) was added. Finally, DIMAD (1.178 g, $8.07 \times 10^{-3}$M) was washed into the solution with tetrahydrofuran (10 ml) and the resultant solution was stirred at room temperature for 15 minutes. The solution was evaporated to an oil in vacuo at 33° C. The oil was dissolved in ethyl acetate (50 ml) then washed with an aqueous 1% sodium chloride solution (4X), an aqueous sodium chloride solution (1X), dried over sodium sulfate, filtered and evaporated to give a froth. The froth was chromatographed on silica gel (Merck, 18 g, packed with toluene), using a gradient elution of toluene (800 ml) versus ethyl acetate (800 ml). The chromatography yielded 4.72 g of a white froth which was further purified by HPLC (silica gel column, gradient elution of hexane versus 45% ethyl acetate/hexane then 45% ethyl acetate/hexane versus 50% ethyl acetate/hexane at a flow rate of 250 ml/minute.) The HPLC procedure yielded 1.209 g of pure product and 1.199 g of impure product. The impure product was rechromatographed on silica gel (15 g, packed in toluene) using a gradient elution of toluene (600 ml) versus 90% ethyl acetate/toluene (600 ml) to give an additional 0.737 g of pure product, para-nitrobenzyl 7-(R)-phenoxyacetamido-3-(but-2'-yn-4'-yloxy)-3-cephem-4-carboxylate: n.m.r. (60 MHz, CDCl$_3$): δ1.87 (m, 3, methyl protons), 3.47 (s, 2, C-2 protons), 4.67 (s, 2, methylene protons of phenoxyacetamido group), 4.77 (m, 2, methylene protons of butynyloxy group), 5.10 (d, J=4, 1, C-6 proton), 5.35 (m, 2, methylene protons of p-nitrobenzyl group), 5.67 (dd, J=4, 8, 1, C-7 protons); f.d.m.s.: M=537; i.r.: (CHCl$_3$), 2250, 1778 cm$^{-1}$.

Example 7

Benzhydryl 7-(R)-[2'-(R)-2'-(N-(t-butylcarbamato))-2'-phenylacetamido]-3-(but-2'-yn-4'-yloxy)-3-cephem-4-carboxylate

Under an argon atmosphere, benzhydryl 7-(R)-[(2'R)-2'-(N-(t-butylcarbamato)-2'-phenylacetamido]-3-hydroxy-3-cephem-4-carboxylate (1.174 g, $1.43 \times 10^{-3}$M), was dissolved in dry tetrahydrofuran (approx. 10 ml). Triphenylphosphine (0.375 g, $1.43 \times 10^{-3}$M), a THF solution (approx. 5 ml) of but-2-yn-4-ylol (0.100 g, $1.43 \times 10^{-3}$M) and a THF solution (5 ml) of DIMAD (0.209 g, $1.453 \times 10^{-3}$M) were added sequentially. The solution was stirred at room temperature for 45 minutes then washed with water (3X), aqueous sodium chloride solution (1X), dried over sodium sulfate, filtered and evaporated to dryness. The residue was chromatographed on silica gel (8 g, packed with toluene) eluting with a gradient of toluene (500 ml) versus 1:1 ethyl acetate:toluene (500 ml) to yield 514 mg, 53.8% of benzhydryl 7-(R)-(2'R)-2'-(N-(t-butylcarbamato))-2'-phenylacetamido]-3-(but-2'-yn-4'-yloxy)-3-cephem-4-carboxylate: n.m.r. (90 MHz, CDCl$_3$): δ1.4 (s, 9, protons of t-butyl group) s, 1.76 (m, 3, methyl group), 3.2 (m, 2, C-2 proton), 4.44 (m, 2, methylene protons of butynyloxy group), 4.92 (d, J=4, 1, C-6 proton), 5.1 (m, 1, methine protons of phenylacetamido group), 5.56 (dd, J=4, 8, 1, C-7 proton), 5.72 (d, J=6, 1, proton on nitrogen of carbamato group); f.d.m.s. M=668.

Example 8

Para-nitrobenzyl 7-(R)-phenoxyacetamido-3-(1'-phenylprop-1'-yn-3'-yloxy)-3-cephem-4-carboxylate

Under an argon atmosphere, para-nitrobenzyl 7-(R)-phenoxyacetamido-3-hydroxy-3-cephem-4-carboxylate acetic acid solvate (0.546 g, $1.0 \times 10^{-3}$M) was dissolved in dried tetrahydrofuran (15 ml) followed by the sequential addition of triphenylphosphine (0.315 g, $1.2 \times 10^{-3}$M) and a tetrahydrofuran solution (10 ml) of 1-phenylprop-1-yn-3-ol (0.159 g, $1.2 \times 10^{-3}$M). A tetrahydrofuran solution (5 ml) of DIMAD (0.175 g, $1.2 \times 10^{-3}$M) was added to the stirred solution. The solution was stirred for 20 minutes at room temperature evaporated to dryness in vacuo at 35° C. The residue was then dissolved in ethyl acetate (50 ml) and the solution was washed with water (4X), aqueous sodium chloride solution (1X), dried over sodium sulfate, filtered and evaporated to dryness. The residue was chromatographed on silica gel (8.0 g, packed with toluene) eluting with a gradient of toluene (500 ml) versus ethyl acetate (500 ml) to yield 0.443 g, 74% of para-nitrobenzyl 7-(R)-phenoxyacetamido-3-(1'-phenylprop-1'-yn-3'-yloxy)-3-cephem-4-carboxylate: n.m.r. (60 MHz, CDCl$_3$): δ3.52 (s, 2, C-2 protons), 4.55 (s, 2, methylene protons of phenoxyacetamido group), 5.02 (d, J=4, 1, C-6 proton), 5.30 (m, 2, methylene protons of para-nitrobenzyl group), 5.64 (dd, J=4, 8, 1, C-7 proton); f.d.m.s.: M=599; i.r. (CHCl$_3$): 1776 cm$^{-1}$.

Example 9

Benzhydryl 7(R)-[(2'R)-2'-(N-(t-butylcarbamato))-2'-phenylacetamido]-3-(1'-phenylprop-1'-yn-3'-yloxy)-3-cephem-4-carboxylate

Under an argon atmosphere, benzhydryl 7-(R)-[(2'R)-2'-(N-(t-butylcarbamato))-2'-phenylacetamido]-3-hydroxy-3-cephem-4-carboxylate (1.231 g, 0.002M) and triphenylphosphine (0.577 g, 0.0022M) were dissolved in dry tetrahydrofuran (15 ml) then 1-phenylprop-1-yn-3-ol (0.291 g, 0.0022M) was added and the resultant solution was cooled in an ice bath. DIMAD (0.321 g, 0.0022M) was washed into the cooled solution with THF (5 ml). The solution was stirred at room temperature for 20 minutes, then evaporated in vacuo at 35° C. to an oil. The oil was dissolved in ethyl acetate and the solution was washed with cold water (4X), sodium chloride solution (1X), dried over sodium sulfate, filtered and evaporated to dryness. The resultant residue was chromatographed on silica gel (8 g, packed with toluene) using a gradient elution of toluene (500 ml) versus 20% ethyl acetate/toluene (500 ml). The product-containing fractions were combined to 0.199 g of pure product. The remaining fractions containing impure product were combined and rechromatographed on the silica gel column, eluting with a gradient of toluene (500 ml) versus 10% ethyl acetate/toluene. An additional 0.278 g of product was obtained from the second chromatography, giving a total of 477 mg, 32.7% yield of benzhydryl 7-(R)-[2'(R)-2'-(N-(t-butylcarbamato))-2'-phenylacetamido]-3-(1'-phenylprop-1'-yn-3'-yloxy)-3-cephem-4-carboxylate: n.m.r. (90 MHz, CDCl$_3$): δ1.40 (s, 9, protons of t-butyl group), 3.20 (m, 2, C-2 protons), 4.68 (m, 2, methylene protons of phenylpropargyloxy group), 4.88 (d, J=4, 1, C-6 protons), 5.2 (d, J=6, 1, methine proton of phenylacetamido group), 5.6 (dd, J=4, 6, 1, C-7 proton), 5.68 (d, J=6, 1, proton on nitrogen of carbamato group); f.d.m.s.: M=730.

Example 10

Para-nitrobenzyl 7-(R)-phenoxyacetamido-3-(methyl but-4'-yloxy-2'-ynoate)-3-cephem-4-carboxylate Under an argon atmosphere, para-nitrobenzyl 7-(R)-phenoxyacetamido-3-hydroxy-3-cephem-4-carboxylate (0.712 g, 1.47×10$^{-3}$M) was dissolved in dry tetrahydrofuran (15 ml). To this stirred solution was added sequentially triphenylphosphine (0.423 g, 1.61×10$^{-3}$M) and a tetrahydrofuran solution (5 ml) of methyl 4-hydroxybut-2-ynoate (0.251 g, 2.20×10$^{-3}$M). DIMAD (0.236 g, 1.61×10$^{-3}$M) was washed into the solution with THF (5 ml). The solution was stirred at room temperature for 35 minutes then evaporated to dryness in vacuo at 30° C. The residue was taken up in ethyl acetate (20 ml) then washed with 1% aqueous sodium chloride solution (4X), aqueous sodium chloride solution (1X), dried over sodium chloride, filtered and evaporated to dryness. The residue was chromatographed on silica gel (8 g, packed in toluene) eluting with a gradient of toluene (400 ml) versus ethyl acetate (400 ml) to give 0.308 g of pure product and 0.132 g of impure product. After rechromatographing the impure product, a 0.374 g yield of para-nitrobenzyl 7-(R)-phenoxyacetamido-3-(methyl but-4'-yloxy-2'-ynoate)-3-cephem-4-carboxylate was realized: (60 MHz, CDCl$_3$): 4.55 (s, 2, methylene protons of the phenoxyacetamido group), 4.77 (s, 2, methylene protons of methylbut-4'-yloxy-2'-ynoate protons), 5.03 (d, J=4, 1, C-6 proton), 5.33 (br. s, 2, methylene protons of para-nitrobenzyl group), 5.73 (dd, J=4, 8, 1, C-7 proton).

Example 11

7-(R)-Phenoxyacetamido-3-(prop-1'-yn-3'-yloxy)-3-cephem-4-carboxylic acid

Para-nitrobenzyl 7-(R)-phenoxyacetamido-3-(prop-1'-yn-3'-yloxy)-3-cephem-4-carboxylate (4.88 g, 9.32×10$^{-3}$M) was dissolved in acetonitrile (60 ml). Water (60 ml) was added and the solution was warmed in a water bath to 40° C. Sodium bicarbonate (6.265 g, 7.46×10$^{-2}$M) was added and the solution was stirred at 40° C. for 3 minutes. Sodium dithionite (6.492 g, 3.73×10$^{-2}$M) was added portion-wise over a 3 minute period. The solution was stirred at 40° C. for 5 minutes then the acetonitrile was removed in vacuo at 35° C. Ethyl acetate was added and the resultant mixture was cooled in an acetone/carbon dioxide slush bath. The mixture was acidified with 1N hydrochloric acid then filtered through celite to remove the resultant yellow polymer. The layers were separated and the aqueous layer was reextracted twice with ethyl acetate. The ethyl acetate layers were combined, washed with water (3X), and extracted with aqueous sodium bicarbonate solution (3X). The aqueous layers were combined and washed with ethyl acetate (1X). The combined aqueous layers were then layered with ethyl acetate and the mixture was cooled in an acetone/carbon dioxide slush bath with stirring. The mixture was acidified with 3N hydrochloric acid. The layers were separated and the aqueous layer was reextracted with ethyl acetate. The ethyl acetate layers were combined, washed with aqueous sodium chloride solution (1X), dried over sodium sulfate, filtered and evaporated to dryness to yield 0.861 g, 24% of 7-(R)-phenoxyacetamido-3-(prop-1'-yn-3'-yloxy)-3-cephem-4-carboxylic acid.

Example 12

7-(R)-[2'-(R)-2'-amino-2'-phenylacetamido]-3-(prop-1'-yn-3'-yloxy)-3-cephem-4-carboxylic acid zwitterion

Procedure A

Under an argon atmosphere, para-nitrobenzyl 7-(R)-[2'-(R)-2'-(N-(t-butylcarbamato))-2-phenylacetamido]-3-(prop-1'-yn-3'-yloxy)-3-cephem-4-carboxylate (0.638 g, 1.02×10$^{-3}$M) was dissolved in acetonitrile (10 ml) then water (8 ml) was added. The solution was warmed to 40° C. Water (2 ml) and sodium bicarbonate (0.859 g, 1.02×10$^{-2}$M) was added and the solution was stirred at 40° C. for 5 minutes. Sodium dithionite (0.712 g, 4.09×10$^{-3}$M) was added portion-wise over a 5 minute period. The solution was stirred for 5 minutes at 40° C., cooled to room temperature then the acetonitrile was removed in vacuo at 30° C. The solution was cooled in a carbon dioxide/acetone slush bath, ethyl acetate was added and the mixture was acidified with 1N hydrochloric acid. The layers were separated and the aqueous layer was extracted with ethyl acetate. The ethyl acetate layers were combined, washed with aqueous sodium chloride solution (1X), dried over sodium sulfate, filtered and evaporated to a foam. The foam, under an argon atmosphere, was treated with triethylsilane (approx. 2 ml) followed by 98% formic acid (approx. 5 ml) and the resultant mixture was stirred at room temperature for 1 hour. The mixture was evaporated to dryness in vacuo at 30° C., then azeotropically distilled with dichloromethane to yield a foam. The foam was combined with the product of a prior repetition of the above procedure and subjected to HPLC purification (reversed phase column, a gradient of 1% acetic acid in water versus 30% acetonitrile and 1% acetic acid in water) give 186 mg, 38% yield of product. This product was redissolved in distilled water, filtered through celite and lyophilized to give 7-(R)-[2'-(R)-2'-amino-2'-phenylacetamido]-3-(prop-1'-yn-3'-yloxy)-3-cephem-4-carboxylic acid zwitterion: n.m.r. (90 MHz, D$_2$O): 3.08 (m, 1, acetylenic proton), 3.36, 3.76 (ABq, J=13, 2, C-2 proton), 4.7 (m, 2, methylene proton of prop-1'-yn-3'-yloxy group), 5.20 (d, J=4, 1, C-6 proton), 5.34 (s, 1, methine proton on phenylacetamido group), 5.70 (d, J=4, 1, C-7 proton).

Procedure B

Under an argom atmosphere, benzhydryl 7-(R)-[2'-(R)-2'-(N-(t-butylcarbamato))-2'-phenylacetamido]-3-(prop-1'-yn-3'-oxy)-3-cephem-4-carboxylate (0.712 g) was treated with triethylsilane (approx. 2 ml) then 98% formic acid (approx. 10 ml) and the resultant solution was stirred at room temperature for 1 hour. The solution was evaporated to dryness in vacuo at 35° C. and azeotropically distilled six times with dichloromethane. The residue from the distillations was purified by HPLC (reversed phase column, eluting with a gradient of 1% acetic acid in water versus 30% acetonitrile and 1% acetic acid in water) to yield 73 mg of 7-(R)-[2'-(R)-

2'-amino-2'-phenylacetamido]-3-(prop-1'-yn-3'-yloxy)-3-cephem-4-carboxylic acid zwitterion (94% purity): n.m.r. as for procedure A immediately above.

Example 13

7-(R)-[2'-(R)-2'-(N-(t-butylcarbamato))-2'-phenylacetamido]-3-(prop-1'-yn-3'-yloxy)-3-cephem-4-carboxylate acid Para-nitrobenzyl 7-(R)-[2'-(R)-2'-(N-(t-butylcarbamato))-2'-phenylacetamido]-3-(prop-1'-yn-3'-yloxy)-3-cephem-4-carboxylate (1.169 g, $1.874 \times 10^{-3}$M) was dissovled in acetonitrile (12 ml). Water (12 ml) was added and the solution was warmed to 40° C. by stirring in a water bath. Sodium bicarbonate (1.89 g, $2.25 \times 10^{-2}$M) was added and the solution was stirred for 1 minute. Sodium dithionite (1.305 g, $7.50 \times 10^{-3}$M) was added portion-wise over two minutes. The resultant slurry was stirred for an additional 5 minutes, water was added and the acetonitrile was evaporated in vacuo at 35° C. The solution was layered with cold ethyl acetate and the mixture was acidified with cold 1N hydrochloric acid. The layers were separated and the aqueous layer was reextracted with ethyl acetate. The ethyl acetate layers were combined, filtered through celite, washed with aqueous sodium chloride solution (1X), dried over sodium sulfate, filtered and evaporated to dryness to give 0.753 g of yellow froth of crude 7-(R)-[2'-(R)-2'-(N-(t-butylcarbamato))-2'-phenylacetamido]-3-(prop-1'-yn-3'-yloxy)-3-cephem-4-carboxylic acid.

Example 14

7-(R)-[2'-(R)-2'-amino-2-(benzothien-3''-yl)acetamido]-3-(prop-1'-yn-3'-yloxy)-3-cephem-4-carboxylic acid zwitterion Under an argon atmosphere, benzhydryl 7-(R)-[2'-(R)-2'-(N-(t-butylcarbamato))-2'-(benzothien-3''-yl)acetamido]-3-(prop-1'-yn-3'-yloxy)-3-cephem-4-carboxylate (0.382 g) is treated with triethylsilane (approx. 2 ml) then 98% formic acid (approx. 6 ml) and the resultant mixture is stirred for 1 hour at room temperature. The mixture is evaporated to dryness in vacuo at 35° C. and the resultant residue is azeotropicly distilled six times with methylene chloride at 35° C. The residue is purified by HPLC (reversed phase column, eluted with an 8 liter gradient of 1% acetic acid in water to 25% acetonitrile and 1% acetic acid in water) to give 130 mg (83.3% purity) of 7-(R)-[2'-(R)-2'-amino-2'-(benzothien-3''-yl)acetamido]-3-(prop-1'-yn-3'-yloxy)-3-cephem-4-carboxylic acid zwitterion: n.m.r. (90 MHz, D$_2$O) δ3.14 (m, 1, acetylinic proton) 3.24, 3.56 (ABq, J=12, 2, C-2 protons), 3.81 (m, 2, methylene protons of propargyloxy group), 4.18 (d, J=4, 1, C-6 proton), 4.60 (d, J=4, 1, C-7 proton), 4.84 (s, 1, methine proton of (benzothien-3''-yl)acetamido group).

Example 15

7-(R)-[2'-(R)-2'-amino-2'-(para-hydroxyphenyl)acetamido]-3-(prop-1'-yn-3'-yloxy)-3-cephem-4-carboxylic acid zwitterion Under an argon atmosphere, benzhydryl 7-(R)-[2'-(R)-2'-(N-(t-butylcarbamato))-2'-(para-hydroxyphenyl)acetamido]-3-(prop-1'-yn-3'-yloxy)-3-cephem-4-carboxylate (777 mg) was treated with triethylsilane (2 ml) then 98% formic acid (6 ml) and the resultant solution was stirred for 1 hour at room temperature. The solution was evaporated to dryness in vacuo at 30° C. The residue was azeotropically distilled with dichloromethane at 35° C. to yield a foam. The foam was purified by HPLC (reversed phase column, eluted with: 1) 8 l of a gradient of 1% acetic acid in water versus 25% acetonitrile and 1% acetic acid in water; 2) 4 l of 25% acetonitrile and 1% acetic acid in water versus 40% acetonitrile and 1% acetic acid in water) to yield 7-(R)-[2'-(R)-2'-amino-2'-(para-hydroxyphenyl)acetamido]-3-(prop-1'-yn-3'-yloxy)-3'-cephem-4-carboxylic acid: n.m.r. (90 MHz, D$_2$O): δ3.18 (m, 1, acetylenic proton), 3.40, 3.92 (ABq, J=12, 2, C-2 protons), 4.92 (m, 2, methylene protons of prop-1'-yn-3'-yloxy), 5.24 (d, J=4, C-6 proton), 5.32 (s, 1, methine proton of (para-hydroxyphenyl)acetamido group), 5.56 (d, J=4, 1, C-7 proton), 7.04, 7.48 (A$_2$B$_2$q, J=6, 4, aromatic protons); f.a.b. m.s.:M=404; i.r. (KBr): 1764 cm$^{-1}$.

Example 16

7-(R)-[2'-(R)-2'-amino-2'-phenylacetamido]-3-(but-2'-yn-4'-yloxy)-3-cephem-4-carboxylic acid Under an argon atmosphere, benzhydryl 7-(R)-[2'-(R)-2'-(N-(t-butylcarbamato))-2'-phenylacetamido]-3-(but-2'-yn-4'-yloxy)-3-cephem-4-carboxylate (0.514 g) was treated with triethylsilane (approx. 2 ml) then 98% formic acid (approx. 6 ml) and the resultant solution was stirred at room temperature for 1 hour. The solution was evaporated to dryness in vacuo at 35° C. then azeotropically distilled six times with methylene chloride in vacuo at 35° C. The resultant residue was purified by HPLC (reverse phase column, eluted with an 8 l gradient of 1% acetic acid in water versus 25% acetonitrile and 1% acetic acid in water) yielding 98 mg of 7-(R)-[2'-(R)-2'-amino-2'-phenylacetamido]-3-(but-2'-yn-4'-yloxy)-3-cephem-4-carboxylate: n.m.r. (90 MHz, D$_2$O): δ1.92 (M, methyl protons of but-2'-yn-4'-yloxy group), 3.3, 3.68 (ABq, C-2 protons), 4.8 (m, methylene protons of but-2'-yn-4'-yloxy group), 5.2 (m, C-6 and C-7 protons and methine proton of phenylacetamido group).

Example 17

Para-nitrobenzyl 7-(R)-amino-3-(prop-1'-yn-3'-yloxy)-3-cephem-4-carboxylate

Under an argon atmosphere, para-nitrobenzyl 7-(R)-phenoxyacetamido-3-(prop-1'-yn-3'-yloxy)-3-cephem-4-carboxylate (2.07 g, $3.95 \times 10^{-3}$M) was dissolved in methylene chloride (approx. 8 ml) and the solution was cooled briefly in a carbon dioxide/acetone slush bath. Pyridine (0.39 ml, $4.86 \times 10^{-3}$M) and phosphorus pentachloride (0.947 g, $4.55 \times 10^{-3}$M) were added and the solution was stirred for 2 hours at room temperature. The solution was cooled briefly in a carbon dioxide/acetone slush bath then isobutanol (1.95 ml, $2.12 \times 10^{-2}$M) was added and the solution was stirred at room temperature for 2 hours. Excess n-heptane was added and decanted from the solution. To the resultant residue was added a mixture of ethyl acetate and aqueous sodium bicarbonate solution. The mixture was stirred to affect dissolution of the residue, the layers were separated, and the ethyl acetate layer was washed once with brine, dried over sodium sulfate, filtered and evaporated to dryness to give 1.406 g, 91% yield of para-nitrobenzyl 7-(R)-amino-3-(prop-1'-yn-3'-yloxy)-3-cephem-4-carboxylate: n.m.r. (60 MHz, CDCl$_3$): δ1.93 (s, 2, amino protons), 2.70 (m, 1, acetylenic proton), 3.60 (ABq, 2, C-2 protons), 4.67 (m, 2, methylene protons of prop-1'-yn-3'-yloxy), 4.75 (d, J=4, 1, C-6 proton), 5.00

(d, J=4, 1, C-7 proton), 5.37 (ABq, 2, methylene protons of para-nitrobenzyl group), 7.60, 8.22 (A$_2$B$_2$q, 4, aromatic proton); f.d.m.s.: M=389; i.r. (CHCl$_3$): 3290, 2130, 1970 cm$^{-1}$.

Example 18

Benzhydryl 7-(R)-amino-3-(prop-1'-yn-3'-yloxy)-3-cephem-4-carboxylate

Under an argon atmosphere, benzhydryl 7-(R)-phenoxyacetamido-3-(prop-1'-yn-3'-yloxy)-3-cephem-4-carboxylate (0.719 g, 1.30×10$^{-3}$M) was dissolved in methylene chloride (approx. 3 ml) and the solution was cooled briefly in a carbon dioxide/acetone slush bath. Pyridine (0.13 ml, 1.59×10$^{-3}$M) then phosphorus pentachloride (0.310 g, 1.49×10$^{-3}$M) was added and the solution was stirred for 2 hours at room temperature. After cooling the solution briefly in a carbon dioxide/acetone slush bath, isobutanol (0.64 ml, 6.94×10$^{-3}$M) was added and the mixture was stirred at room temperature for 1 hour. Excess n-heptane was added then decanted from the solution. The resultant crystals were dissolved in a mixture of ethyl acetate and aqueous sodium bicarbonate. The layers of the mixture were separated, and the ethyl acetate layer was washed with aqueous sodium bicarbonate solution (1X), brine (1X), dried over sodium sulfate, filtered and evaporated to dryness to yield benzhydryl 7-(R)-amino-3-(prop-1'-yn-3'-yloxy)-3-cephem-4-carboxylate: n.m.r. (90 MHz, CDCl$_3$): δ1.84 (s, 2, amino protons), 2.52 (m, 1, acetylenic proton), 3.48 (ABq, 2, C-2 protons), 4.48 (m, 2, methylene protons of prop-1'-yn-3'-yloxy), 4.60 (d, J=4, 1, C-6 proton), 4.88 (d, J=4, 1, C-7 proton), 6.92 (s, 1, methine protons of benzhydryl group), 7.32, (m, 10, aromatic protons); f.d.m.s.: M=420; i.r. (CHCl$_3$): 3285, 2120, 1765 cm$^{-1}$.

Example 19 para-Nitrobenzyl 7-(R)-amino-3-(but-2'-yn-4-yloxy)-3-cephem-4-carboxylate

Under an argon atmosphere, para-nitrobenzyl 7-(R)-phenoxyacetamido-3-(but-2'-yn-4'-yloxy)-3-cephem-4-carboxylate (1.960 g, 3.65×10$^{-3}$M) was partially dissolved in methylene chloride (15 ml). The suspension was cooled briefly in a carbon dioxide/acetone slush bath then pyridine (0.36 ml, 4.48×10$^{-3}$M) was washed in with methylene chloride (5 ml). Phosphorus pentachloride (0.873 g, 4.19×10$^{-3}$M) was added and the suspension was stirred at room temperature for two hours, at the end of which time the suspension had become a solution. The solution was cooled briefly in a carbon dioxide/acetone slush bath and isobutanol (1.80 ml, 1.95×10$^{-2}$M) was added. The solution was stirred at room temperature for one hour, cooled in a carbon dioxide/acetone slush bath then excess n-heptane was added. The mixture was filtered and a white solid was collected. The solid was dried in vacuo for 15 minutes at 50° C. to give 1.988 g of the hydrochloride salt of the title compound.

The hydrochloride salt was dissolved in a mixture of saturated aqueous sodium bicarbonate solution and ethyl acetate. The layers were separated and the ethyl acetate layer was washed with saturated aqueous sodium chloride solution (1X), dried over sodium sulfate, filtered and evaporated to a gum (1.988 g). The gum was chromatographed on silica gel (15 g, packed with toluene) eluting with a gradient of 15% ethyl acetate/toluene (600 ml) versus ethyl acetate (600 ml). The product-containing fractions were combined to give a yellow froth (0.974 g, 66.2% yield) of para-nitrobenzyl 7-(R)-amino-3-(but-2'-yn-4'-yloxy)-3-cephem-4-carboxylate: n.m.r. (60 MHz, CDCl$_3$): δ1.90 (m, 3, methyl protons of but-2'-yn-4'-yloxy group), 3.47, 3.68 (ABq, J=16, 2, C-2 protons), 4.62 (m, 2, methylene protons of but-2'-yn-4'-yloxy group), 4.70 (d, J=4, 1, C-6 protons), 4.97 (d, J=4, 1, C-7 proton), 5.33 (ABq, 2, methylene protons of para-nitrobenzyl group), 7.57, 8.17 (A$_2$B$_2$q, 4, aromatic protons); i.r. (CHCl$_3$): 2240, 1770 cm$^{-1}$.

Example 20 para-Nitrobenzyl 7-(R)-phenoxyacetamido-3-(but-1'-yn-4'-yloxy)-3-cephem-4-carboxylate Under an argon atmosphere, para-nitrobenzyl 7-(R)-phenoxyacetamido-3-hydroxy-3-cephem-4-carboxylate (0.546 g, 1.0×10$^{-3}$M) was dissolved in THF (10 ml). Triphenylphosphine (0.289 g, 1.1×10$^{-3}$M) then but-1-yn-4-ylol (0.077 g, 1.1×10$^{-3}$M) was added. DIMAD (0.161 g, 1.1×10$^{-3}$M) was washed into the solution with THF (5 ml). The solution was stirred at room temperature for 30 minutes then evaporated to dryness at 35° C. The residue from the evaporation was taken up in ethyl acetate (approx. 20 ml) and the solution was washed with brine (4X), saturated aqueous sodium chloride solution (1X), dried over sodium sulfate, filtered and evaporated to a tan froth (0.841 g). The froth was chromatographed over silica gel (E. Merck, 8.0 g, packed with toluene). The silica gel column was eluted with a gradient of toluene (400 ml) versus 70% ethyl acetate/toluene (400 ml). The product-containing fraction were combined to give 0.353 g of para-nitrobenzyl 7-(R)-phenoxyacetamido-3-(but-1'-yn-4'-yloxy)-3-cephem-4-carboxylate: n.m.r. (60 MHz, CDCl$_3$): δ2.05 (m, 1, acetylenic proton), 2.57 (m, 2, C-3' methylene protons of but-1'-yn-4'-yloxy group), 3.43 (br. s, 2, C-2 protons), 4.1 (m, 2, C-4' methylene protons of but-1'-yn-4'-yloxy group), 4.58 (s, 2, methylene protons of phenoxyacetamido group), 5.07 (d, J=4, 1, C-6 proton), 5.33 (br. s, 2, methylene protons of para-nitrobenzyl group), 5.63 (dd, J=4, 8, 1, C-7 proton); f.d.m.s.: M=537; i.r. (CHCl$_3$): 3300, 1778 cm$^{-1}$.

Example 21

Benzhydryl 7-(R)-[(2'R)-2'-(N-(t-butylcarbamato))-2'-phenylacetamido]-3-(but-1'-yn-4'-yloxy)-3-cephem-4-carboxylate Under an argon atmosphere, benzhydryl 7-(R)-[(2'R)-2'-(N-(t-butylcarbamato))-2'-phenylacetamido]-3-hydroxy-3-cephem-4-carboxylate (2.001 g, 3.25×10$^{-3}$M) and triphenylphosphine (0.852 g, 3.25×10$^{-3}$M) were dissolved in THF (8 ml). But-1'-yn-4'-ylol (0.228 g, 3.25×10$^{-3}$M) was added and DIMAD (0.475 g, 3.25×10$^{-3}$)M) was washed in with THF (2 ml). The solution was stirred for 15 minutes at room temperature. The solution was diluted with ethyl acetate, washed with water (3X), brine (1X), saturated aqueous sodium chloride solution (1X), dried over sodium sulfate, filtered and evaporated to dryness. The residue from the evaporation was chromatographed on silica gel 15 g, packed with toluene) eluting with a gradient of toluene (600 ml) versus ethyl acetate (600 ml). The product-containing fractions were combined to yield 1.247 g of benzhydryl 7-(R)-[(2'R)-2'-(N-(t-butyl-carbamato))-2'-phenylacetamido]-3-(but-1'-yn-4'-yloxy)-3-cephem-4-carboxylate: n.m.r. (90 MHz, CDCl$_3$) δ1.4 (s, 9, protons of t-butyl group), 2.00 (M, 1, acetylenic proton), 2.40 (M, 2, C-2' methylene protons of but-1'-yn-4'-yloxy group), 3.00, 3.20 (ABq, J=13, 2, C-2 protons), 3.84 (m, 2, C-4' methylene protons of but-1'-yn-4'-yloxy group), 4.96 (d, J=4, 1, C-6 proton), 5.20 (d, J=5, 1, methine proton of phenylacetamido group), 5.56 (dd, J=4, 7, 1, C-7 proton), 5.76 (d, J=5, 1, proton on nitrogen of t-butylcarbamato group); f.d.m.s.: 667, 506.

Example 22

7-(R)-[(2'R)-2'-amino-2'-phenylacetamido]-3-(but-1'-yn-4'-yloxy)-3-cephem-4-carboxylic acid zwitterion Benzhydryl 7-(R)-[(2'R)-2'-(N-(t-butylcarbamato))-2'-phenylacetamido]-3-(but-1'-yn-4'-yloxy)-3-cephem-4-carboxylate (1.247 g) was treated with triethylsilane (total of 4 ml) then 98% formic acid (total of 10 ml) under an argon atmosphere. The solution was stirred for 2.5 hours at room temperature. The solution was evaporated to dryness at 30° C. and the resultant residue was repeatedly azeotropically distilled with methylene chloride to give a yellow foam. The foam was purified by HPLC (reverse phase column, eluting with a gradient (8 l) of 1% acetic acid in water versus 40% acetonitrile and 1% acetic acid in water) to yield 512 mg, 98.4% yield of 7-(R)-[(2'R)-2'-amino-2'-phenylacetamido]-3-(but-1'-yn-4'-yloxy)-3-cephem-4-carboxylic acid zwitterion: n.m.r. (90 MHz, D$_2$O): δ2.52 (m, 1, acetylenic proton), 2.64 (m, 2, C-2' methylene protons of but-1'-yn-4'-yloxy group), 3.32, 3.72 (ABq, J=13, 2, C-2 protons), 4.12 (m, 2, C-4' methylene protons of but-1'-yn-4'-yloxy group), 5.20 (d, J=4, 1, C-6 proton), 5.34 (s, 1, methine proton of phenylacetamido group), 5.66 (d, J=4, 1, C-7 proton).

I claim:
1. A compound of the formula:

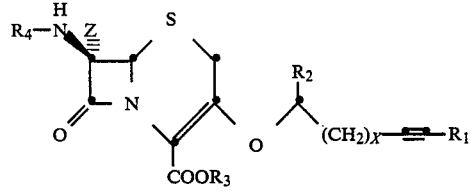

wherein:
R$_1$ is hydrogen, C$_1$ to C$_4$ alkyl, C$_1$ to C$_4$ alkoxycarbonyl, C$_1$ to C$_4$ alkylthio, or phenylthio or halo;
R$_2$ is hydrogen, C$_1$ to C$_4$ alkyl, phenyl, benzyl or phenethyl;
R$_3$ is hydrogen, a carboxy protecting group, a pharmaceutically acceptable, non-toxic salt of the carboxy group, a hydrate of said salt, or a non-toxic, metabolically labile ester of the carboxy group; and
R$_4$ is
(a) hydrogen, or a salt of said compound;
(b) an amino-protected group;
(c) a group of the formula:

wherein
R$_5$ is
(i) 1,4-cyclohexadienyl, 1-cyclohexenyl, phenyl or substituted phenyl wherein the substituents are 1 or 2 halogens, hydroxy, protected hydroxy, nitro, cyano, trifluoromethyl, C$_1$ to C$_4$ alkyl, C$_1$ to C$_4$ alkoxy, carboxy, protected carboxy, carboxymethyl, protected carboxymethyl, hydroxymethyl, protected hydroxymethyl, aminomethyl, protected aminomethyl, or N-(methylsulfonylamino);
(ii) an arylalkyl group of the formula

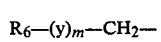

wherein y is O or S, m is 0 or 1, R$_6$ is R$_5$ as defined above, and when m is 0, R$_6$ is also 2-thienyl, 3-thienyl, 2-furyl, 3-furyl, 1-tetrazolyl, 5-tetrazolyl, 2-thiazolyl, 2-aminothiazol-4-yl, or 2-(protected amino)thiazol-4-yl; or
(iii) a substituted arylalkyl group of the formula

wherein
R$_7$ is R$_6$ as defined above, 2- or 3-indolyl, a substituted 2- or 3-indolyl group of the formula

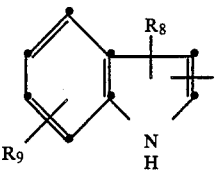

in which
R$_8$ and R$_9$ independently are hydrogen, halo, hydroxy, protected hydroxy, C$_1$ to C$_4$ alkyl, C$_1$ to C$_4$ alkoxy, nitro, amino, protected amino, C$_1$ to C$_4$ alkanoylamino, C$_1$ to C$_4$ alkylsulfonylamino, or when R$_8$ and R$_9$ are on adjacent carbons, they may be taken together to form methylenedioxy, 2- or 3-benzothienyl, 2- or 3-substituted benzothienyl of the formula

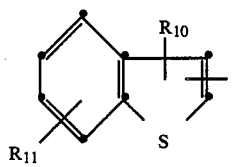

in which
R$_{10}$ and R$_{11}$ are independently hydrogen, halo, hydroxy, protected hydroxy, C$_1$ to C$_4$ alkyl, C$_1$ to C$_4$ alkoxy, nitro, amino, protected amino, C$_1$ to C$_4$ alkanoylamino, C$_1$ to C$_4$ alkylsulfonylamino, and when R$_{10}$ and R$_{11}$ are on adjacent carbon atoms, they can be taken together to form methylenedioxy; 1- or 2-naphthyl, substituted 1- or 2-naphthyl of the formula

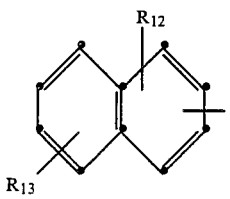

wherein

R$_{12}$ and R$_{13}$ are independently hydrogen, halo, hydroxy, protected hydroxy, C$_1$ to C$_4$ alkyl, C$_1$ to C$_4$ alkoxy, nitro, amino, protected amino, C$_1$ to C$_4$ alkanoylamino, C$_1$ to C$_4$ alkylsulfonylamino, or when R$_{12}$ and R$_{13}$ are on adjacent carbon atoms, they can be taken together to form methylenedioxy;

W is hydroxy, protected hydroxy, carboxy, a carboxy salt, protected carboxy, amino, a salt of said amino compound, or protected amino; provided that, when W is other than amino, a salt of said amino compound or protected amino, R$_7$ is other than 2 or 3-indolyl, substituted 2- or 3-indolyl, 2- or 3-benzothienyl, 2- or 3-substituted benzothienyl, 1- or 2-naphthyl, or substituted 1- or 2-naphthyl; and wherein X is 0 to 4 and Z is hydrogen or methoxy.

2. A compound of claim 1, wherein R$_4$ is hydrogen or a salt of said amino compound.

3. A compound of claim 2, wherein X is zero.

4. A compound of claim 3, wherein R$_2$ is hydrogen and R$_1$ is hydrogen, methyl, phenyl, or methoxycarbonyl.

5. A compound of claim 4, wherein R$_3$ is para-nitrobenzyl, benzhydryl, para-methoxybenzyl, hydrogen, a pharmaceutically-acceptable, non-toxic salt of the carboxylate group or a hydrate of said salt and Z is hydrogen.

6. A compound of claim 5, wherein R$_4$ is hydrogen, or a hydrochloride salt or a para-toluenesulfonate salt of said amino compound.

7. A compound of claim 6, wherein R$_4$ is hydrogen, or the hydrochloride salt of said amino compound, R$_3$ is para-nitrobenzyl or benzhydryl and R$_1$ is hydrogen.

8. A compound of claim 6, wherein R$_4$ is hydrogen or a hydrochloride salt of said amino compound, R$_3$ is para-nitrobenzyl and R$_1$ is methyl.

9. A compound of claim 2, wherein X is from 1 to 4.

10. A compound of claim 9, wherein X is one.

11. A compound of claim 10, wherein R$_2$ is hydrogen and R$_1$ is hydrogen, methyl, phenyl or methoxycarbonyl.

12. A compound of claim 11, wherein R$_3$ is para-nitrobenzyl, benzhydryl, para-methoxybenzyl, hydrogen, a pharmaceutically-acceptable, non-toxic salt of the carboxylate group or a hydrate of said salt and Z is hydrogen.

13. A compound of claim 12, wherein R$_4$ is hydrogen, or a hydrochloride salt or a para-toluenesulfonate salt of said amino compound.

14. A compound of claim 1, wherein R$_4$ is an amino-protecting group.

15. A compound of claim 14, wherein X is zero.

16. A compound of claim 15, wherein R$_2$ is hydrogen and R$_1$ is hydrogen, methyl, phenyl or methoxycarbonyl.

17. A compound of claim 16, wherein R$_3$ is para-nitrobenzyl, benzhydryl, para-methoxybenzyl, hydrogen, a pharmaceutically-acceptable, non-toxic salt of the carboxylate group or a hydrate of said salt and Z is hydrogen.

18. A compound of claim 17, wherein R$_4$ is t-butoxycarbonyl, benzyloxycarbonyl, 2,2,2-trichloroethoxycarbonyl, para-methoxycarbonyl, trityl, allyloxycarbonyl, or trimethylsilyl.

19. A compound of claim 14, wherein X is 1 to 4.

20. A compound of claim 19, wherein X is one.

21. A compound of claim 20, wherein R$_2$ is hydrogen and R$_1$ is hydrogen, methyl, phenyl, or methoxycarbonyl.

22. A compound of claim 21, wherein R$_3$ is para-nitrobenzyl, benzhydryl, para-methoxybenzyl, hydrogen, a pharmaceutically-acceptable, non-toxic salt of the carboxylate group or a hydrate of said salt and Z is hydrogen.

23. A compound of claim 22, wherein R$_4$ is t-butoxycarbonyl, benzyloxycarbonyl, 2,2,2-trichloroethoxycarbonyl, para-methoxycarbonyl, trityl, allyloxycarbonyl or trimethylsilyl.

24. A compound of claim 1, wherein R$_4$ is a group of the formula

wherein R$_5$ is an arylalkyl group of the formula

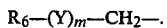

25. A compound of claim 24, wherein X is zero.

26. A compound of claim 25, wherein R$_2$ is hydrogen, R$_1$ is hydrogen, methyl, phenyl or methoxycarbonyl and Z is hydrogen.

27. A compound of claim 26, wherein m is zero, R$_6$ is phenyl, 2-thienyl, 3-thienyl, 2-furyl, 3-furyl, 1-tetrazolyl, 5-tetrazolyl, 2-thiazolyl, 2-aminothiazol-4-yl or 2-(protected amino)thiazol-4-yl and R$_3$ is hydrogen, sodium ion, potassium ion, para-nitrobenzyl or benzhydryl.

28. A compound of claim 26, wherein m is one and R$_3$ is hydrogen, sodium ion, potassium ion, paranitrobenzyl or benzhydryl.

29. A compound of claim 28, wherein Y is O and R$_6$ is phenyl.

30. A compound of claim 24, wherein X is from 1 to 4.

31. A compound of claim 30, wherein X is 1.

32. A compound of claim 31, wherein R$_1$ is hydrogen, methyl, phenyl or methoxycarbonyl, R$_2$ is hydrogen and Z is hydrogen.

33. A compound of claim 32, wherein m is zero, R$_6$ is phenyl, 2-thienyl, 3-thienyl, 2-furyl, 3-furyl, 1-tetrazolyl, 5-tetrazolyl, 2-thiazolyl, 2-aminothiazol-4-yl, or 2-(protected amino)thiazol-4-yl, and R$_3$ is hydrogen, sodium ion, potassium ion, para-nitrobenzyl or benzhydryl.

34. A compound of claim 32, wherein m is one and R$_3$ is hydrogen, sodium ion, potassium ion, para-nitrobenzyl or benzhydryl.

35. A compound of claim 34, wherein y is 0 and R$_6$ is phenyl.

36. A compound of claim 1, wherein R$_4$ is a group of the formula 4,604,386

wherein R₅ is a group of the formula

37. A compound of claim 36, wherein X is zero.

38. A compound of claim 37, wherein W is amino, a salt of said amino compound, or protected amino and Z is hydrogen.

39. A compound of claim 38, wherein $R_7$ is phenyl, para-hydroxyphenyl, 2-benzothienyl, 3-benzothienyl, 1-naphthyl, 2-naphthyl, 2-indolyl or 3-indolyl, $R_2$ is hydrogen and $R_1$ is hydrogen, methyl, phenyl or methoxycarbonyl.

40. A compound of claim 39, wherein W is amino or a hydrochloride salt of said amino compound, $R_3$ is hydrogen, or when $R_3$ and W are taken in conjunction to form the zwitterion of said compound.

41. A compound of claim 40, wherein $R_1$ is hydrogen.

42. A compound of claim 41, wherein $R_7$ is phenyl, para-hydroxyphenyl or 3-benzothienyl.

43. A compound of claim 40, wherein $R_1$ is methyl, phenyl or methoxycarbonyl.

44. A compound of claim 43, wherein $R_7$ is phenyl.

45. A compound of claim 39, wherein W is protected amino.

46. A compound of claim 45, wherein W is N-(t-butylcarbamato) and $R_3$ is benzhydryl or para-nitrobenzyl.

47. A compound of claim 46, wherein $R_1$ is hydrogen.

48. A compound of claim 47, wherein $R_7$ is phenyl, para-hydroxyphenyl or 3-benzothienyl.

49. A compound of claim 36, where X is from 1 to 4.

50. A compound of claim 49, wherein X is one.

51. A compound of claim 50, wherein W is amino, a salt of said amino compound or protected amino.

52. A compound of claim 51, wherein $R_7$ is phenyl, para-hydroxyphenyl, 1-naphthyl, 2-naphthyl, 2-indolyl, 3-indolyl, 2-benzothienyl or 3-benzothienyl, and $R_1$, $R_2$ and Z are each hydrogen.

53. A compound of claim 52, wherein W is amino or a hydrochloride salt of said amino compound, $R_3$ is hydrogen, or, when W is amino, W and $R_3$ are taken together to form the zwitterion of said compound.

54. A compound of claim 53, wherein $R_7$ is phenyl, para-hydroxyphenyl or 3-benzothienyl.

55. A compound of claim 52, wherein W is protected amino.

56. A compound of claim 55, wherein W is N-(t-butyl carbamato).

57. A compound of claim 56, wherein $R_3$ is benzhydryl or para-nitrobenzyl and $R_7$ is phenyl, para-hydroxyphenyl or 3-benzothienyl.

58. A pharmaceutical composition useful for the control of gram-positive bacterial infections comprising a suitable vehicle and an antibacterially effective amount of the compound of claim 1, wherein:

$R_3$ is hydrogen, a pharmaceutically-acceptable, non-toxic salt of the carboxy group, a hydrate of said salt, or a non-toxic, metabolically-labile ester of the carboxy group;

$R_4$ is a group of the formula:

wherein
R₅ is
(i) 1,4-cyclohexadienyl, 1-cyclohexenyl, phenyl or substituted phenyl wherein the substituents are 1 or 2 halogens, hydroxy, nitro, cyano, trifluoromethyl, $C_1$ to $C_4$ alkyl, $C_1$ to $C_4$ alkoxy, carboxy, carboxymethyl, hydroxymethyl; aminomethyl, or N-(methylsulfonylamino);

(ii) an arylalkyl group of the formula

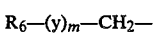

wherein y is O or S, m is 0 or 1, $R_6$ is $R_5$ as defined above, and when m is 0, $R_6$ is also 2-thienyl, 3-thienyl, 2-furyl, 3-furyl, 1-tetrazol, 5-tetrazol, 2-thiazolyl, or 2-aminothiazol-4-yl; or (iii) a substituted arylalkyl group of the formula

wherein
$R_7$ is $R_5$ as defined above, 2- or 3-indolyl, substituted 2- or 3-indolyl of the formula

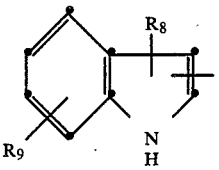

in which
$R_8$ and $R_9$ independently are hydrogen, halo, hydroxy, $C_1$ to $C_4$ alkyl, $C_1$ to $C_4$ alkoxy, nitro, amino, $C_1$ to $C_4$ alkanoylamino, $C_1$ to $C_4$ alkylsulfonylamino, or when $R_8$ and $R_9$ are on adjacent carbons, they may be taken together to form methylenedioxy; 2- or 3-benzothienyl, 2- or 3-substituted benzothienyl of the formula

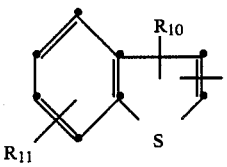

in which
$R_{10}$ and $R_{11}$ are independently hydrogen, halo, hydroxy, $C_1$ to $C_4$ alkyl, $C_1$ to $C_4$ alkoxy, nitro, amino, $C_1$ to $C_4$ alkanoylamino, $C_1$ to $C_4$ alkylsulfonylamino, and when $R_{10}$ and $R_{11}$ are on adjacent carbon atoms, they can be taken together to form methylenedioxy; 1- or 2-naphthyl, substituted 1- or 2-naphthyl of the formula

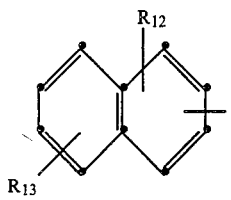

wherein $R_{12}$ and $R_{13}$ are independently hydrogen, halo, hydroxy, $C_1$ to $C_4$ alkyl, $C_1$ to $C_4$ alkoxy, nitro, amino, $C_1$ to $C_4$ alkanoylamino, $C_1$ to $C_4$ alkylsulfonylamino, or when $R_{12}$ and $R_{13}$ are on adjacent carbon atoms, they can be taken together to form methylenedioxy; and W is hydroxy, formyloxy, carboxy, a carboxy salt, amino, or a salt of said amino compound, provided that, when W is other than amino or a salt of said amino compound, $R_7$ is other than 2 or 3-indolyl, substituted 2- or 3-indolyl, 2- or 3-benzothienyl, 2- or 3-substituted benzothienyl, 1- or 2-naphthyl, or substituted 1- or 2-naphthyl; and wherein X is 0 to 4 and Z is hydrogen or methoxy.

59. A pharmaceutical composition of claim 58, wherein $R_3$ is hydrogen, sodium cation or potassium cation, $R_4$ is a group of the formula:

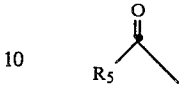

wherein $R_5$ is a group of the formula

and $R_7$ is phenyl, para-hydroxyphenyl or 3-benzothienyl and W is amino or a salt of said amino compound, or when W is amino and $R_3$ is hydrogen they are taken in conjunction to form the zwitterion.

* * * * *